US012714126B2

(12) United States Patent
Moslemy et al.

(10) Patent No.: US 12,714,126 B2
(45) Date of Patent: Aug. 25, 2026

(54) THERMALLY-RESISTANT WAX MATRIX PARTICLES FOR ENZYME ENCAPSULATION

(71) Applicant: DANISCO US INC., Palo Alto, CA (US)

(72) Inventors: Peyman Moslemy, Sunnyvale, CA (US); Nathaniel T. Becker, Burlingame, CA (US); Luke Barnard, East Wichel (GB)

(73) Assignee: DANISCO US INC., Palo Alto, CA (US)

( * ) Notice: Subject to any disclaimer, the term of this patent is extended or adjusted under 35 U.S.C. 154(b) by 524 days.

(21) Appl. No.: 16/967,777

(22) PCT Filed: Feb. 8, 2018

(86) PCT No.: PCT/US2018/017367
§ 371 (c)(1),
(2) Date: Jul. 20, 2023

(87) PCT Pub. No.: WO2019/156670
PCT Pub. Date: Aug. 15, 2019

(65) Prior Publication Data

US 2020/0359656 A1 Nov. 19, 2020

(51) Int. Cl.

| | |
|---|---|
| ***A23K 20/158*** | (2016.01) |
| ***A23K 20/189*** | (2016.01) |
| ***A23K 20/24*** | (2016.01) |
| ***A23K 40/10*** | (2016.01) |
| ***A23K 40/30*** | (2016.01) |

(Continued)

(52) U.S. Cl.
CPC .......... *A23K 20/158* (2016.05); *A23K 20/189* (2016.05); *A23K 20/24* (2016.05); *A23K 40/10* (2016.05); *A23K 40/30* (2016.05); *C11D 3/38672* (2013.01); *C12N 11/04* (2013.01)

(58) Field of Classification Search
CPC .... A23K 20/158; A23K 20/189; A23K 20/24; A23K 40/10; A23K 40/30; A23K 50/30; A23K 50/75; C11D 3/38672; C12N 11/04
See application file for complete search history.

(56) References Cited

U.S. PATENT DOCUMENTS 8,597,641 B2 * 12/2013 Harz ..................... A23K 40/10 435/177
2005/0163765 A1 * 7/2005 Andela ................. A23K 40/30 424/94.2

(Continued)

FOREIGN PATENT DOCUMENTS

EP 1586241 A1 * 10/2005 .......... A23K 20/158

OTHER PUBLICATIONS

Marcus (2017, Low Molecular Weight Polyethylene Waxes, https://web.archive.org/web/20171113143435/https://www.marcusoil.com/product/low-molecular-weight-polyethylene-waxes/) (Year: 2017).*

(Continued)

*Primary Examiner* — Michele L Jacobson
*Assistant Examiner* — Carrie Glimm

(57) ABSTRACT

Described are compositions and methods relating to thermally-resistant wax matrix particles for enzyme encapsulation. The particles are well-suited for animal feed applications, particularly those involving steam pelleting.

14 Claims, 16 Drawing Sheets

(51) Int. Cl.
*C11D 3/386* (2006.01)
*C12N 11/04* (2006.01)

(56) References Cited

U.S. PATENT DOCUMENTS

| | | | | |
|---|---|---|---|---|
| 2006/0078598 | A1 * | 4/2006 | Jobe | A23K 40/30<br>426/625 |
| 2008/0031998 | A1 * | 2/2008 | Marcussen | A23K 40/20<br>426/453 |
| 2009/0220646 | A1 * | 9/2009 | Scott Street | C12N 9/16<br>426/54 |
| 2009/0274795 | A1 * | 11/2009 | Lohscheidt | C12Y 301/03026<br>435/196 |

OTHER PUBLICATIONS

Manitoba (2013, Water Content and Water Activity: Two Factors that Affect Food Safety, https://web.archive.org/web/20131114141607/http://gov.mb.ca/agriculture/food-safety/at-the-food-processor/water-content-water-activity.html) (Year: 2013).*

* cited by examiner

| Effect test | *P* value |
|---|---|
| Enzyme | 0.9762 |
| Analysed Phytase | <.0001 |
| Enzyme * Analysed Phytase | 0.0761 |

| Effect test | *P* value |
|---|---|
| Enzyme | 0.2948 |
| Analysed Phytase | <.0001 |
| Enzyme * Analysed Phytase | 0.5745 |

| Effect test | *P* value |
|---|---|
| Enzyme | 0.7247 |
| Analysed Phytase | 0.0005 |
| Enzyme * Analysed Phytase | 0.9069 |

| Effect test | P value |
|---|---|
| Enzyme | 0.1785 |
| Analysed Phytase | <.0001 |
| Enzyme * Analysed Phytase | 0.0096 |

| Effect test | *P* value |
|---|---|
| Enzyme | 0.0208 |
| Analysed Phytase | <.0001 |
| Enzyme * Analysed Phytase | 0.0064 |

| Effect test | *P* value |
|---|---|
| Enzyme | 0.5995 |
| Analysed Phytase | <.0001 |
| Enzyme * Analysed Phytase | 0.7769 |

| Effect test | *P* value |
|---|---|
| Enzyme | 0.6925 |
| Analysed Phytase | <.0001 |
| Enzyme * Analysed Phytase | 0.4802 |

| Effect test | *P* value |
|---|---|
| Enzyme | 0.5609 |
| Analysed Phytase | <.0001 |
| Enzyme * Analysed Phytase | 0.2486 |

| Effect test | *P* value |
|---|---|
| Enzyme | 0.8318 |
| Analysed Phytase | 0.0001 |
| Enzyme * Analysed Phytase | 0.9996 |

| Effect test | *P* value |
|---|---|
| Enzyme | 0.0439 |
| Analysed Phytase | <.0001 |
| Enzyme * Analysed Phytase | 0.0913 |

THERMALLY-RESISTANT WAX MATRIX PARTICLES FOR ENZYME ENCAPSULATION

TECHNICAL FIELD

The present compositions and methods relate to thermally-resistant wax matrix particles for enzyme encapsulation. The particles are well-suited for animal feed applications, particularly those involving steam pelleting.

BACKGROUND

Existing commercial processes for producing granules include prilling, high shear granulation, and fluidized bed spray-coating. Prilling of enzyme granules is described in U.S. Pat. No. 4,016,040. In prilling, also known as spray-chilling or spray-congealing, a molten liquid is atomized and then solidified into particles. Various atomization methods can be used, including spray nozzle atomization, centrifugal nozzle atomization and spinning disk atomization. (see, e.g., U.S. Pat. Nos. 7,261,529 and 7,758,778). When prilling is applied to enzyme encapsulation, a dry enzyme powder is blended with a molten hydrophilic binder such as a nonionic surfactant and the mixture is atomized into droplets using a spray nozzle or disk into cool air, such that it solidifies into substantially spherical, water dispersible solid particles or "prills" containing the dispersed enzyme powder. The binder in these prills is hydrophilic and water soluble or dispersible, allowing the enzyme to be released into detergent wash water once the binder dissolves.

High shear granulation of enzymes suitable for use in pelletized animal feed is described in, e.g., WO 92/12645. Enzyme is first granulated with various binders and fillers, e.g., to produce a so-called "T-granule" (described in U.S. Pat. No. 4,106,991). The T-granule is then overcoated with an agent comprising a high-melting fat or wax, typically also further including an inorganic filler such as kaolin, magnesium silicate or calcium carbonate. The high melting fat or wax is specified as a glycerol ester or other waxy substance with a melting point between 30 and 100° C.

Enzyme granules with multiple protective coating layers can be produced using coating processes such as fluidized bed spray coating. For example, U.S. 2006/040394 describes a process for producing a granule stable to steam pelleting that includes a moisture hydrating coating and a moisture barrier applied to an enzyme core. The moisture hydrating coating can be a layer that includes sodium sulfate and the moisture barrier can be a layer that includes polyvinyl alcohol and talc.

A process for protecting enzyme granules with thick coatings is described in WO 01/25412. The coating is referred to as a "shell unit," which is applied over a "core unit," such that the ratio between the diameter of the resulting granule and the diameter of the core unit is at least 1.1. Enzyme activity is limited solely to the core unit; the shell unit is specified as being "substantially enzyme free," that is, containing less than 5 mg enzyme/gram shell. The shell unit has no specified limitations on its chemical composition and may include either hydrophilic or hydrophobic materials such as polymers or waxes. When used to protect enzymes in steam pelleting of feeds, it is specified that the shell units should have an overall composition that will melt under the pelleting conditions, and should have a melting temperature within the range of 70-120° C.

While the processes and formulations described in the above-cited patents provide a certain degree of protection to enzymes against inactivation by high temperature and moisture, such as that encountered in steam pelleting or storage in animal feed or detergents, these technologies suffer from certain drawbacks. In the prior applications of prilling, the binders used in the matrix will dissolve or will melt at the high temperature and moist conditions such as those used in steam pelleting, or spray drying of laundry detergent, leaving the enzyme highly vulnerable to denaturation by hot vapor or water. In the case of the other technologies cited, protection of the enzyme requires the addition of thick coatings that are substantially free of enzyme. Such coatings may be readily applied to larger enzyme cores, i.e., those with median diameters greater than about 300 microns, but they are not efficiently applied to smaller particles It is, therefore, desirable to identify a granulation technology that can protect enzymes against high temperature and moisture, provide adequate release or bioavailability in aqueous based applications such as animal feed or detergents, and yet avoid the need to apply a protective coating or barrier layer. There is also a need for a granulation technology capable of producing particles with high active enzyme concentrations that are smaller than 500 microns in diameter, providing both low cost and improved distribution when mixed into end products such as animal feed or detergents.

SUMMARY

The present compositions and methods relate to thermally-resistant wax matrix particles for enzyme encapsulation. The wax matrix particles are well-suited for food and animal feed applications, particularly those involving steam pelleting. Aspects and embodiments of the compositions and methods are described in the following, independently-numbered paragraphs.

1. In one aspect, a particle comprising particulates containing one or more enzymes dispersed within a high-melting wax matrix is provided.

2. In some embodiments of the particle of paragraph 1, the wax matrix comprises a water-insoluble wax.

3. In some embodiments of the particle of paragraph 1 or 2, the wax has a peak maximum melting point greater than 100° C., optionally greater than 110° C., and even optionally greater than 120° C.

4. In some embodiments of the particle of any of paragraphs 1-3, the wax has an onset melting point of at least 100° C. and a peak maximum melting point of at least 110° C.

5. In some embodiments of the particle of any of paragraphs 1-3, the wax has an onset melting point of at least 110° C. and a peak maximum melting point of at least 120° C.

6. In some embodiments of the particle of any of paragraphs 1-5, the wax has a melt viscosity of less than 500 centipoises at temperatures within 25° C. above the wax melting temperature.

7. In some embodiments of the particle of any of paragraphs 1-5, the wax has a weight average molecular weight of less than 3,000 and a polydispersity index of less than 3.

8. In some embodiments of the particle of any of paragraphs 1-5, the $ECR_{(40,140)}$ is less than 20%, and preferably less than 15%.

9. In some embodiments of the particle according to any of paragraphs 1-8, the enzyme is at least one of amylase, cellulase, phytase, protease, or xylanase.

10. In some embodiments, the particle according to any of paragraphs 1-9 comprises an active enzyme payload of greater than 5% wt/wt, and a water activity of less than 0.3.

11. In some embodiments of the particle according to any of paragraphs 1-10, the enzyme particulates range from about 1 to about 250 micrometers.

12. In some embodiments, the particle according to any of paragraphs 1-10 comprises a water content of less than 5% wt/wt, and a water activity of less than 0.4.

13. In some embodiments of the particle according to any of paragraphs 1-12, the particles range from about 100 to about 500 micrometers.

14. In some embodiments of the particle of paragraph 13, the particles size ranges from about 212 to about 425 micrometers.

15. In some embodiments of the particle of paragraph 13, the particles size ranges from about 212 to about 300 micrometers.

16. In some embodiments of the particle according to any of paragraphs 1-15, the enzyme particulates are produced with any of spray drying, spray chilling, dry granulation, wet granulation, or fluid bed granulation.

17. In some embodiments, the particle according to any of paragraphs 1-16 comprise a filler ingredient selected from a group of mineral substances consisting of limestone, mica, clay, and titanium oxide.

18. In some embodiments of the particle according to any one of paragraphs 1-17, wax is selected from a group of polymer waxes consisting of polyethylene wax, oxidized polyethylene wax, polypropylene wax, Fischer-Tropsch wax, carboxylic acid salt wax, or a mixture thereof.

19. In some embodiments of the particle according to any one of paragraphs 1-17, wax is a polyethylene wax.

20. In some embodiments of the particle according to any one of paragraphs 1-17, wax is selected from a group of waxes consisting of aluminum stearate, calcium stearate, magnesium stearate, zinc behenate, zinc laurate, zinc stearate, or a mixture thereof.

21. In some embodiments of the particle according to any one of paragraphs 1-17, wax is zinc stearate.

22. In some embodiments of the particle according to any of paragraphs 18-21, the particle comprises a polyterpene resin, a rosin resin, damar gum, or a mixture of the said resins.

23. In some embodiments of the particle according to paragraph 21, the particle comprises a polyterpene resin, a rosin resin, a damar gum, or a mixture of the said resins.

24. In another aspect, a method for preparing a particle comprising enzyme particulates dispersed within a high-melting wax matrix is provided, comprising:

(a) dispersing a dry enzyme powder in a molten wax to provide an enzyme-wax suspension;
(b) atomizing the enzyme-wax suspension to form discrete droplets; and
(c) cooling, solidifying and collecting the enzyme-wax particles.

25. In some embodiments of the method of paragraph 24, the resulting enzyme-wax particles are the particles according to any of paragraphs 1-23.

26. In another aspect, a method for improving poultry or porcine growth is provided, comprising introducing a particle according to any of paragraphs 1-23 into the diet of the animal, and measuring an improvement in growth relative to control animal not treated with such a particle.

These and other aspects and embodiments of the compositions and methods will be apparent from the description and accompanying drawings.

DETAILED DESCRIPTION

I. Introduction—Thermally-Resistant, Wax Matrix Particles

Figure 1:
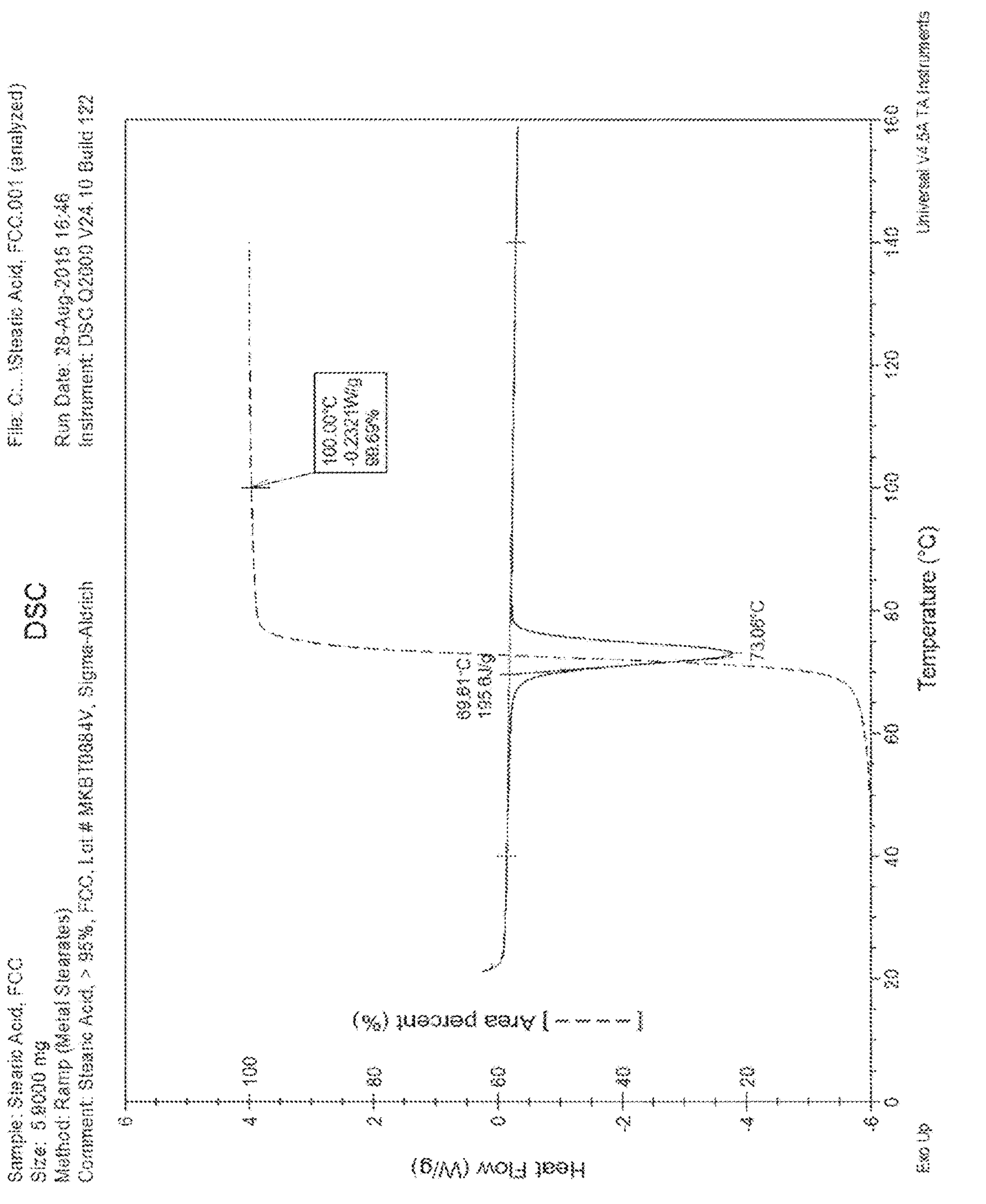
FIG. 1 shows a DSC thermogram of commercial stearic acid, demonstrating an $ECR_{(40,140)}$=99.69%.
Figure 2:
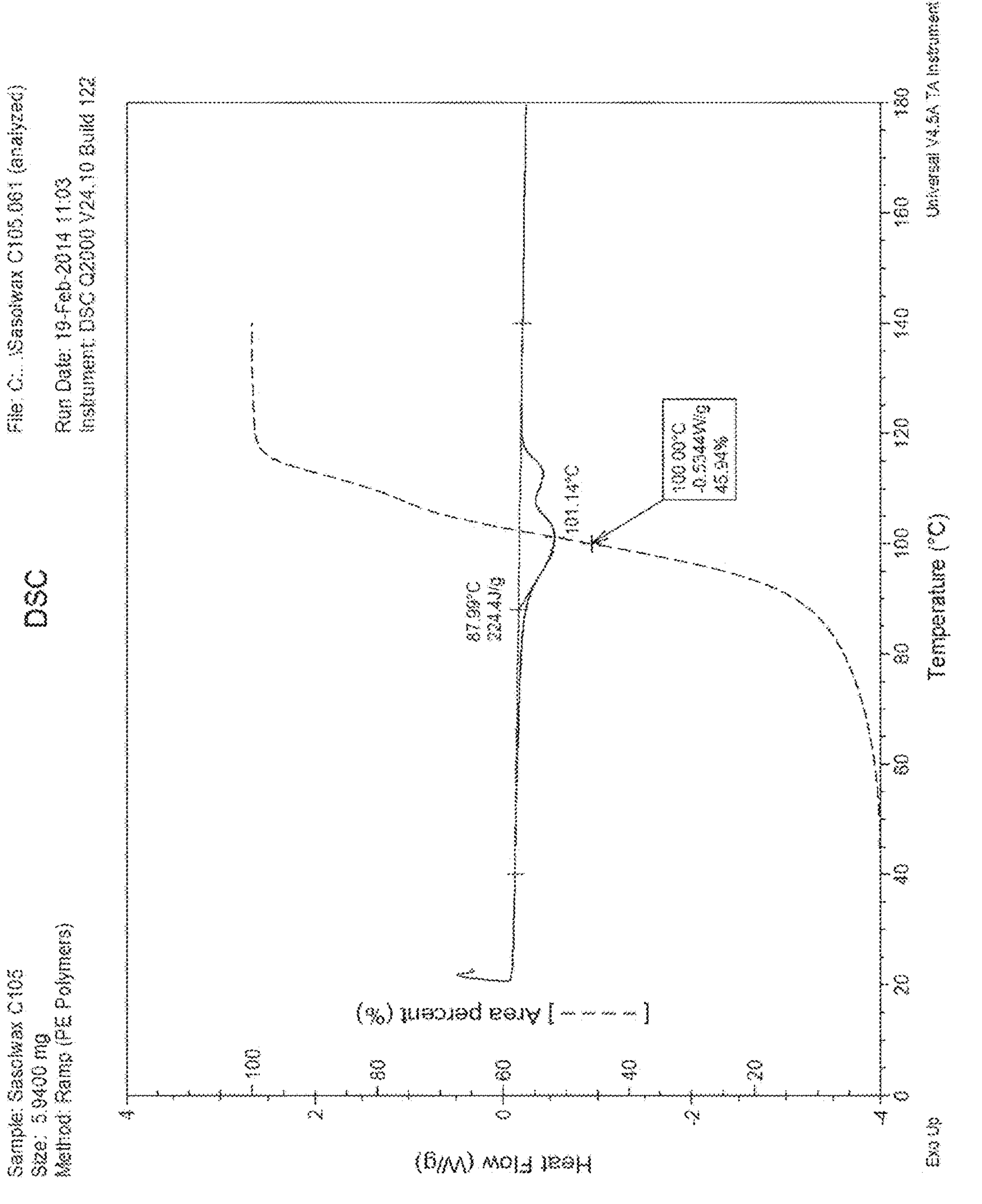
FIG. 2 shows a DSC thermogram of commercial Fischer-Tropsch sax, Sasolwax C 105, demonstrating an $ECR_{(40,140)}$ of 45.94%.
Figure 3:
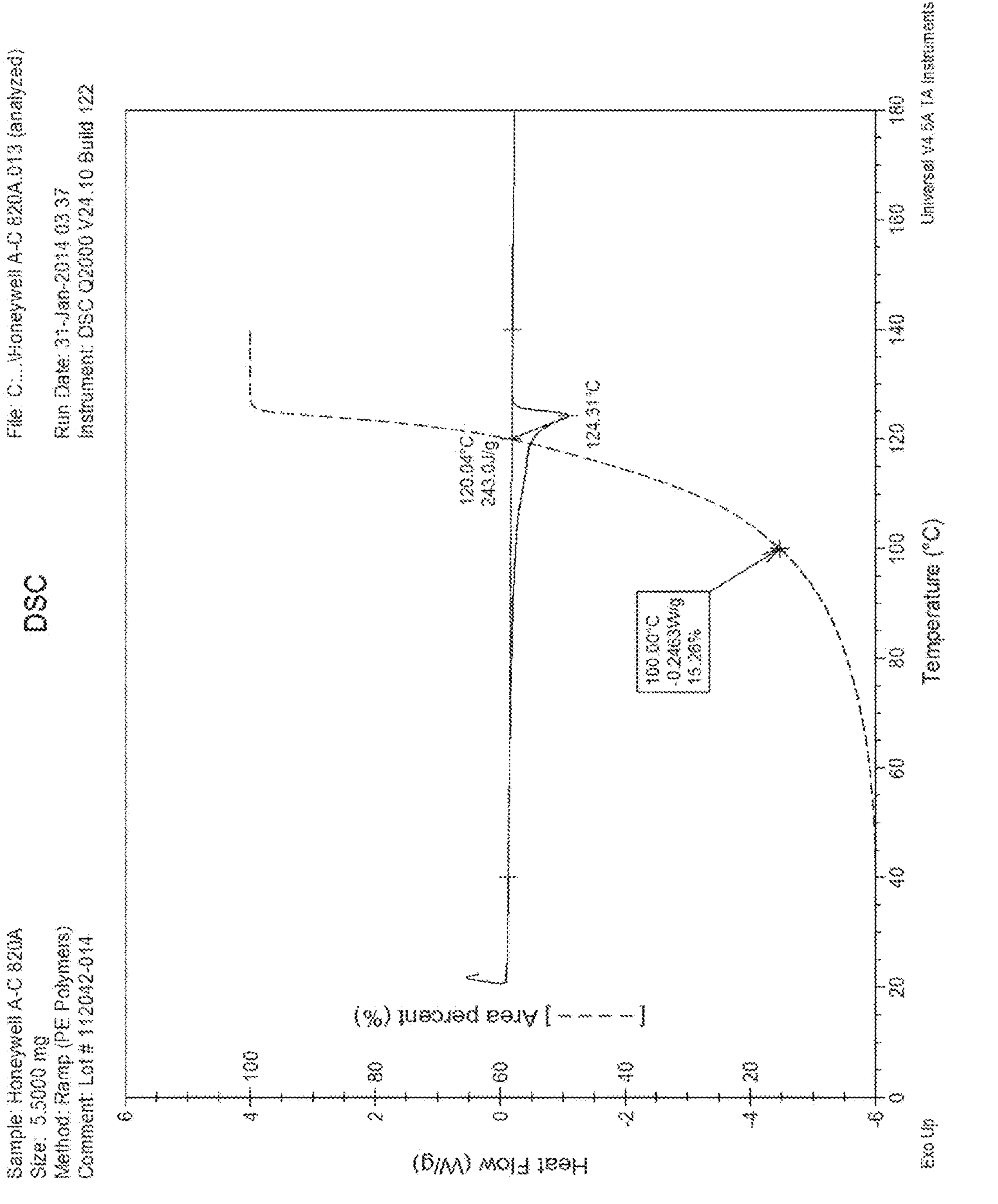
FIG. 3 shows a DSC thermogram of commercial polyethylene homopolymer wax, Honeywell A-C® 820A, demonstrating an $ECR_{(40,140)}$ of 15.26%
Figure 4:
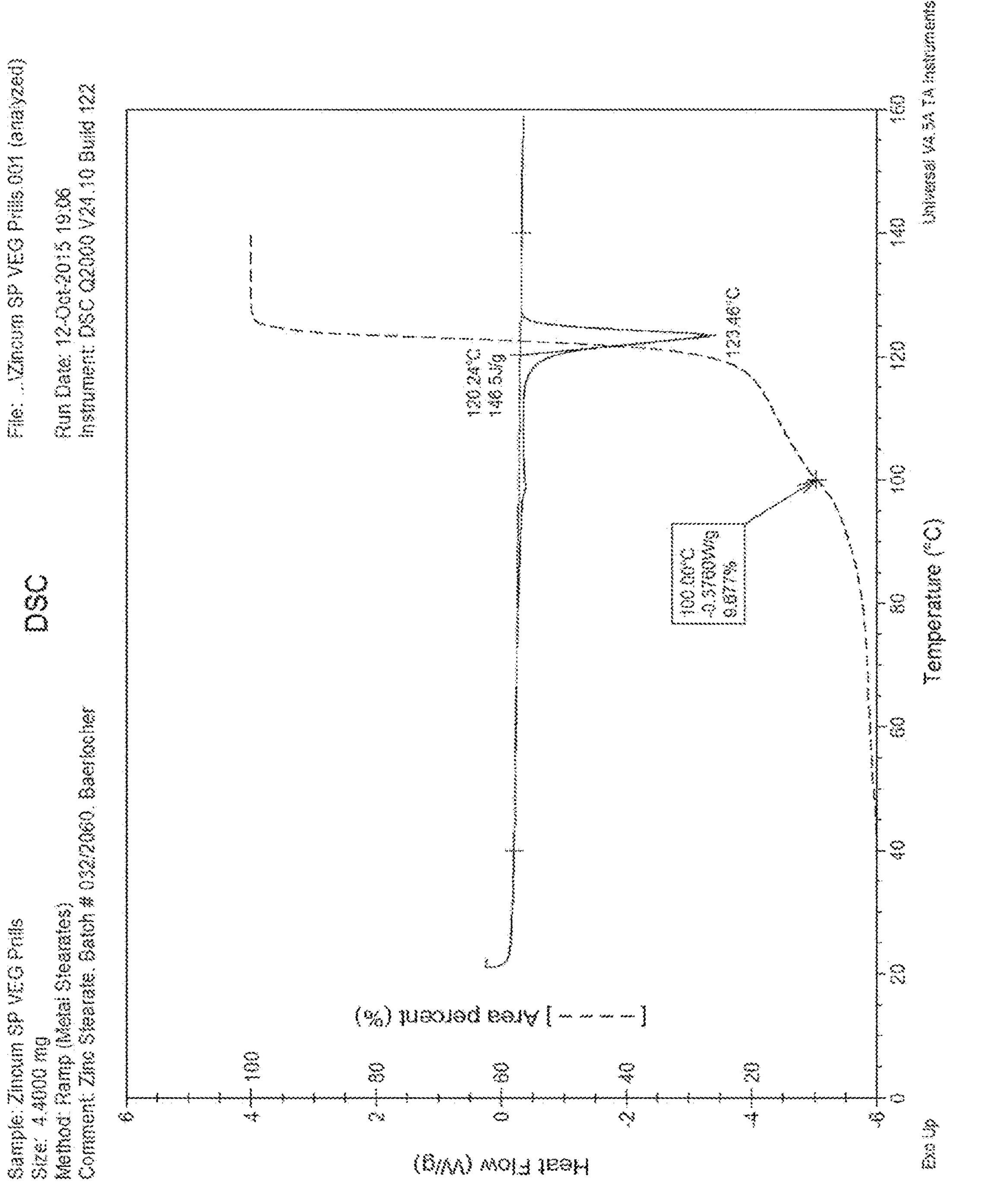
FIG. 4 shows a DSC thermogram of commercial zinc stearate, ZINCUM® SP VEG, demonstrating an $ECR_{(40,140)}$ of 9.68%.
Figure 5:
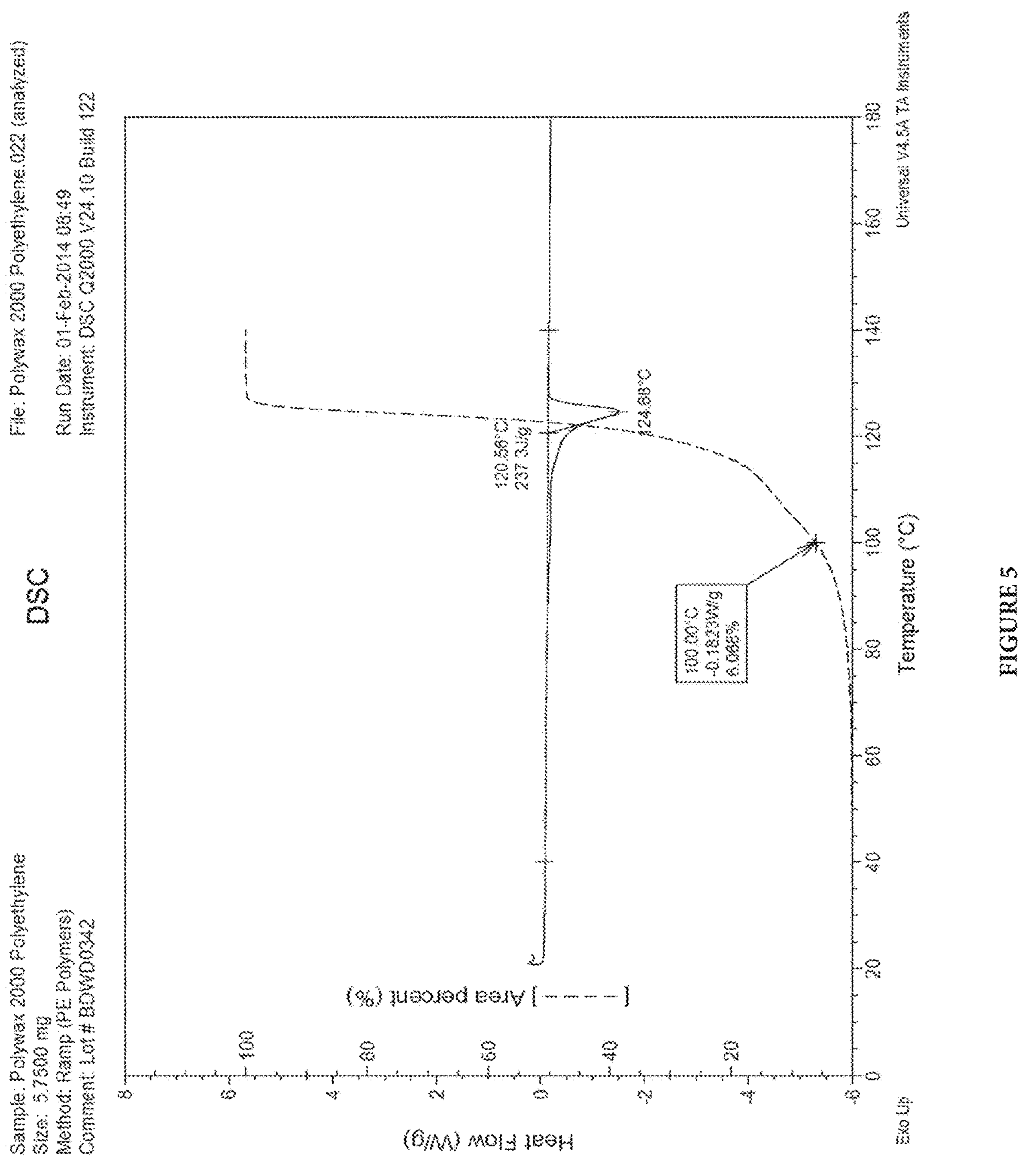
FIG. 5 shows a DSC thermogram of commercial polyethylene homopolymer wax, POLYWAX™ 2000, demonstrating an $ECR_{(40,140)}$ of 6.07%.

The present compositions and methods relate to protecting an enzyme against inactivation under conditions of high temperature and moisture, by encapsulating the enzyme within a particle comprising a high melting point wax matrix. The resulting thermally-resistant, wax matrix particles (herein referred to as "TRWMP") are coating-free, substantially-spherical, microgranules, that are smaller than about 500 microns in average diameter, and contain active enzymes at payloads greater than 5% w/w. In some embodiments, the encapsulated enzymes retain 70% of the original enzyme activity upon exposure to a temperature 95° C. for 30 seconds in a typical animal feed pelleting process, and can provide acceptable enzyme bioavailability when incorporated into animal feed. In some embodiments, the particles provide acceptable enzyme bioavailability in food, animal feed and other agricultural applications.

II. Definitions and Abbreviations

As used herein, a "wax" is defined as any hydrocarbon, fatty acid, fatty alcohol, or salt or ester thereof, that is insoluble in water but soluble in non-polar organic solvents. A comprehensive definition of wax has been drawn up in Europe by the Deutsche Gesellschaft fur Fettwissenschaft (DGF, German Association for Fat Science). According to this definition, waxes (i) have a drop point or melting point above 40° C. (ii) melt without decomposition; (iii) have melt viscosities not exceeding 10,000 mPa·s at 10° C. above the melting point, (iv) exhibit strongly negative temperature dependence in terms of viscosity and do not tend toward stringiness above the melting point, (v) are polishable under slight pressure and have a strongly temperature-dependent consistency and solubility, (vi) are kneadable or hard to brittle, coarse to finely crystalline, transparent to opaque, but not glassy, or highly viscous or liquid at 20° C., (vii) melt between 50° and 90° C. (special waxes, as used in the present compositions and methods, melt at temperatures as high as 200° C.), and form pastes or gels and are poor conductors of heat and electricity (i.e., they are thermal and electrical insulators).

A wax is considered to be "water-insoluble" if its equilibrium solubility in deionized water is less than 0.1% w/w. A wax that is not water-insoluble is herein considered "water-soluble."

A wax is considered to be "low-melting" if it has a peak maximum melting point below 100° C.

A wax is considered to be "high-melting" if it has a peak maximum melting point equal to or above 100° C., preferably above 110° C., and more preferably above 120° C.

As used herein, a "matrix" is a continuous solid phase that surrounds discontinuously dispersed solids. A matrix may be non-porous or porous. A matrix is "porous" if it has channels or pores comprising either open void space or material that can be at least partially dissolved or dispersed upon contact or immersing in water or an aqueous solution, so as to allow the water to penetrate, dissolve, and extract the dispersed solids within the matrix.

As used, herein, "excipients" are inactive components of a product that enhance product properties, e.g., handling, production, or storage stability, without impacting the activity or potency of the product. Although inactive in terms of efficacy, excipients provide beneficial characteristics that allow the enzyme to be delivered to the target application effectively.

Examples of excipients are "fillers" which are used to dilute the active component to adjust potency or reduce formula cost, "binders" which promote cohesion of formula components and or increase the overall physical strength of the granule, "disintegrants" which expand upon contact with water, aiding release of the active from the formulation, "glidants" which promote interparticle friction and powder flow through process equipment, "lubricants" which reduce friction and adhesion between formulation components and process equipment, "preservatives" which prevent or limit the loss of enzyme activity by acting as stabilization aids (e.g., moisture sinks, free-radical scavengers), and "absorbents" which preferentially absorb moisture to protect the enzyme component of the granule.

As used herein, the term "bioavailability" refers to the availability of encapsulated enzymes to an animal gut when an animal feed product containing the encapsulated enzymes is ingested by an animal. In some embodiments, the term "bioavailability" refers to the availability of encapsulated enzymes to the dirt-cleaning media in cleaning applications, such as laundry, dish or hard-surface cleaning.

The following abbreviations are used:

% w/w weight percent
AUC area under heat flow curve
ATTD apparent total tract digestibility
avail available
avg average
AvP available phosphorus
BW body weight
Ca calcium
cm centimeters
CP crude protein
Cys cysteine
$d_{10}$ diameter of 10% of particles on a cumulative volume-size distribution curve
$d_{50}$ diameter of 50% of particles on a cumulative volume-size distribution curve
$d_{90}$ diameter of 90% of particles on a cumulative volume-size distribution curve
dia diameter
DSC differential scanning calorimetry
dT/dt scanning rate
ECR enthalpy change ratio
F-T Fischer-Tropsch
FTU phytase unit of activity
g gram
h hour
ISO International Organization for Standardization
kcal kilocalories
kg kilogram
L liter
Lys lysine
m meter
m.p. melting point
$m^3$ cubic meter
Met methionine
$M_i$ molecular weight of polymer i
min minute
min minutes
ml millileter
mol mole
mm millimeter
$M_n$ number average molecular weight
mPa milliPascal
$M_w$ mass average molecular weight
n number
NC negative control
$N_i$ number of moles of polymers with molecular weight Mi
nm nanometer
nPP non-phytate phosphate ° C. degree Celsius
PE polyethylene
Pin total intake of phosphorus
Pfo) total fecal output of phosphorus
Px, Px.x applicant's internal formulation identifiers
rpm revolutions per minute
s second
std dev standard deviation
T temperature
t time
Trp tryptophan
vits/TEs vitamins and trace elements
wt/wt weight/weight
@ at
μm micrometer
μmol micromolar III. Waxes Suitable for Preparing TRWMP Waxes suitable for use in the present compositions and methods can be naturally occurring and may be derived from non-fossil biological sources and include but are not limited to: animal waxes such as beeswax, ghedda wax, shellac wax, Chinese insect wax, wool wax; vegetable waxes such as carnauba wax, candelilla wax, ouricury wax, sugarcane wax, Retamo wax, and jojoba wax; animal and vegetable fat-derived long chain linear primary carboxylic acids such as myristic acid, palmitic acid, and stearic acid; mixture of fatty acid derivatives; fatty acid salts such as aluminum, calcium, magnesium and zinc stearates, zinc behenate, and zinc laurate; and vegetable fossil waxes such as montan wax; or they can be derived from petroleum, such as macrocrystalline waxes (paraffin waxes) and microcrystalline waxes (microwaxes), or synthetic, either as a small molecule such as ethylene bis-stearamide or as a macromolecule, i.e. chemically polymerized from monomeric subunits such as Fischer-Tropsch waxes or polyolefin waxes including polyethylene wax, polypropylene wax, and their derivatives.

Commercial examples of long chain carboxylic acids are fatty acid derivatives such as BAEROLUB® A275 (Baerlocher GmbH), LICOMONT® BS 100 (Clariant Corp.) and branched alkane carboxylic acid/salt such as LICOWAX® R 21 (Clariant Corp.).

Examples of metal stearates that are commercially available include aluminum tri/di strearate such as ALUGEL® (Baerlocher GmbH), calcium stearate such as CEASIT® (Baerlocher GmbH) and COAD® 13-LD Ca Stearate (Norac, Inc.), magnesium strearate such as MAGNESIUM-STEARAT® (Baerlocher GmbH), zinc stearate such as ZINCUM® SMS Veg, ZINCUM® SP Veg, ZINCUM® TX Veg (Baerlocher GmbH), COAD® 30 Zn Stearate and COAD® 33 Zn Stearate (Norac, Inc.), and co-reacted calcium/zinc stearate NORSTAB® 50 CaZn (Norac, Inc.).

Commercial examples of zinc behenate and zinc laurate include, respectively, ZINCUM® BE and ZINCLAURAT® Techn. R.G. (Baerlocher GmbH).

Commerical examples of ethylene bis-stearamide include BAEROLUB® L-AK (Baerlocher GmbH), LICOWAX® C and LICOLUB® FA 1 (Clariant Corp.) and Ross Wax 140 (Frank B. Ross Co.).

Fischer-Tropsch waxes are commercially available under different trade names including Ceraflour (BYK USA), SARAWAX® (Shell/Baker Hughes, Inc.), SASOLWAX® (SASOL® Wax North America Corp.), and VESTOWAX® (Evonik Degussa Corp.).

Polyethylene waxes are marketed under several different trade names including BAEROLUB® PA-L (Baerlocher GmbH), CERAFLOUR® (BYK USA), DEUREX® E (Deurex AG), EXCEREX™ and HI-WAX™ (Mitsui Chemicals, Inc.), EPOLENE® (Westlake Chemical Corp.), HONEYWELL A-C® (Honeywell International, Inc.), LICOCENE® PE and LICOWAX® PE (Clariant Corp.), NEOWAX™ (Yasuhara Chemical Co., Ltd.), Polywax™ (Baker Hughes, Inc.), and VISCOWAX® (Innospec Leuna GmbH).

Oxidized polyethylene waxes are commercially available under multiple trade names including DEUREX® EO (Deurex AG), LICOWAX® PED (Clariant Corp.), PETROLITE™ (Baker Hughes, Inc.), and VISCOWAX® (Innospec Leuna GmbH).

Polypropylene waxes are marketed under several different trade names including HI-WAX™ (Mitsui Chemicals, Inc.) and LICOCENE® PP (Clariant Corp.).

In certain embodiments, the TRWMP may include a natural, bio-based, or synthetic resin, including but not limited to rosin resins, polyterpene resins, and damar gum.

Rosin resins are based on natural resources, for example renewable pine stumpwood. Refined and modified wood rosins are commercially available through Pinova, Inc., under multiple trade names including PENTALYN® FC, PENTALYN® H and HA, PEXALYN®, STAYBELITE®, STAYBELITE® A, STAYBELITE® Ester and Ester A, and FORAL®. Other commercial products offered by Kraton Corp. (formerly Arizona Chemical Co., LLC) include those marketed under trade names of SYLVATAC™ RE and SYLVALITE™ RE.

Polyterpene resins are based on natural and renewable feedstocks, including poly(α-pinene), poly(β-pinene), poly (d-limonene), and mixtures thereof. Commercial examples of polyterpene resins include those offered by Pinova, Inc., under several trade names including PINOVA® Resin, PICCOLYTE® A, PICCOLYTE® C, PICCOLYTE® F, and PICCOLYTE® S series, and those available through Kraton Corp. (formerly Arizona Chemical Co., LLC), under the trade name SYLVARES™ TR.

Damar gum is the dried exudation from cultivated trees of *Agathis* spp., *Hopea* spp., and/or *Shorea* spp. It consists of a complex mixture of acidic and neutral triterpenoid resins together with polysaccharide material. Many of triterpenes are low molecular weight compounds such as dammarane, dammarenolic acid, oleanane, oleanonic acid, etc., but damar gum also contains a polymeric fraction, composed of polycadinene.

Suitable waxes include those having a peak maximum melting point, i.e., above 100° C., preferably above 110° C., and more preferably above 120° C. Unlike small molecules the molecular weight of a polymer wax is not one unique value. Rather, a given polymer generally exhibits polydispersity, i.e., a distribution of molecular weights, which depends on the way the polymer is manufactured. The distribution of molecular weight is commonly presented by an average molecular weight. Polymer properties such as melting point are function of molecular weight distribution, and thus depend on average molecular weight. The number average molecular weight ($M_n$) and the mass average molecular weight ($M_w$) are defined by the following equations:

$$M_n = \frac{\Sigma N_i M_i}{\Sigma Ni}$$

-continued $$M_w = \frac{\Sigma N_i M_i^2}{\Sigma N_i M_i}$$

where $N_i$ is the number of moles of polymers with molecular weight $M_i$.

Polymer waxes suitable for the present compositions and methods should have a mass average molecular weight ($M_w$) between 1000 and 5000 Da (g/mol), preferably between 1,800 and 4,800 Da, and more preferably between 2000 and 3000 Da. The polymer waxes of this invention should have narrow molecular weight distributions with polydispersity index ($M_w/M_n$) of less than 3, preferably less than 2, more preferably less than 1.5, and most preferably less than 1.2.

Waxes suitable for the present compositions and methods also have a suitable enthalpy change ratio (ECR) defined as follows:

$$ECR_{(t0,tf)}=100\%\times AUC_{(t0,100)}/AUC_{(t0,t)}$$

where $t_0$ and $t_f$ are the initial and final scanning temperatures during differential scanning calorimetry (i.e., a DSC thermogram), and the AUC is the area under the curve of the DSC thermogram.

For example, $ECR_{(40,140)}$ is the 100% times the ratio of the area under a DSC thermogram between 40° C. and 100° C. and the area under the DSC thermogram between 40° C. and 140° C.: $ECR_{(40,140)}=100\%\times AUC_{(40,100)}/AUC_{(40,140)}$.

The ECR can be used as a metric for comparing different wax materials for their potential protective effectiveness in a high-temperature process such as in animal feed pelleting. More specifically, the $ECR_{(40,140)}$ can be used as an indicator of the concentration of low melting hydrocarbons (m.p. <100° C.) in the wax product; a lower amount of low melting hydrocarbons in the wax product corresponds to a smaller $ECR_{(40,140)}$ value. Waxes suitable for the present compositions and methods can be characterized as those with an $ECR_{(40,140)}$ of less than 20%, preferably less than 15%, and more preferably less than 10%.

The present examples illustrate a method for ECR determination using Fischer-Tropsch (F-T) waxes, polyethylene (PE) waxes, zinc stearates, and stearic acid characterized using differential scanning calorimetry (DSC).

For convenience, properties of the present particles are summarized in Table 1.

TABLE 1

Properties of the present particles

| Particle feature | Preferred parameter |
|---|---|
| Peak maximum melting point | >100° C. |
| Onset melting point of wax | ≥100° C. |
| Melt viscosity of wax | <500 centipoises at temperatures within 25° C. above the wax melting temperature |
| Wax average molecular weight | <3,000 |
| Wax polydispersity index | <3 |
| Wax $ECR_{(40, 140)}$ | <20% |
| Enzyme payload | >5% wt/wt |
| Water activity | <0.4 |
| Water content | <5% wt/wt |
| Enzyme particulates size range | 1-500 μm |

IV. Enzymes Suitable for Encapsulation in TRWMP

The present compositions and methods are applicable to many different enzymes. Exemplary enzymes include acyl transferases, α-amylases, β-amylases, α-galactosidases, arabinosidases, aryl esterases, β-galactosidases, carrageenases, catalases, cellobiohydrolases, cellulases, chondroitinases, cutinases, endo-β-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, perhydrolases, peroxidases, peroxygenases, phenoloxidases, phosphatases, phospholipases, phytases, polygalacturonases, proteases, pullulanases, reductases, rhamnogalacturonases, β-glucanases, tannases, transglutaminases, xylan acetyl-esterases, xylanases, xyloglucanases, xylosidases, and combinations, thereof.

Examples of phytases include but are not limited to those from *Escherichia coli, Buttiauxella* sp., *Citrobacter braakii, Peniophora lycii* and *Aspergillus niger*. In some embodiments the protease is one or more of QUANTUM®, QUANTUM® BLUE, PHYZYMEXP™, AXTRA® PHY, RONOZYME™ HIPHOS or NATUPHOS. Phytases are described in, e.g., WO2006038128, US2017143004, US2006141562, US2016362666, US2016289655, U.S. Pat. Nos. 9,365,840, 8,663,963, and US2015159149.

Examples of proteases include but are not limited to subtilisins, such as those derived from *Bacillus* (e.g., subtilisin, lentus, amyloliquefaciens, subtilisin Carlsberg, subtilisin 309, subtilisin 147 and subtilisin 168), including variants as described in, e.g., U.S. Pat. Nos. RE 34,606, 5,955,340, 5,700,676, 6,312,936, and 6,482,628, all of which are incorporated herein by reference. Additional proteases include trypsin (e.g., of porcine or bovine origin) and the *Fusarium* protease described in WO 89/06270. In some embodiments the protease is one or more of MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (DuPont Industrial Biosciences); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Additional proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500,364, 5,855,625, U.S. RE 34,606, 5,955,340, 5,700,676, 6,312,936, and 6,482,628.

Proteases include neutral metalloproteases including those described in WO 07/044993 and WO 09/058661. Other exemplary metalloproteases include nprE, the recombinant form of neutral metalloprotease expressed in *Bacillus subtilis* (see e.g., WO 07/044993), and PMN, the purified neutral metalloprotease from *Bacillus amyloliquefacients*.

Lipases include, but are not limited to *Humicola lanuginosa* lipase (see e.g., EP 258 068, and EP 305 216), *Rhizomucor miehei* lipase (See e.g., EP 238 023), *Candida lipase*, such as *C. antarctica* lipase (e.g., the *C. antarctica* lipase A or B; See e.g., EP 214 761), *Pseudomonas lipases* such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus lipase* (e.g., *B. subtilis* lipase (Dartois et al. (1993) *Biochem. Biophys. Acta* 1131:253-260); *B.*

*stearothermophilus* lipase (see e.g., JP 64/744992); and *B. pumilus* lipase (see e.g., WO 91/16422)).

Additional lipases include *Penicillium camembertii* lipase (Yamaguchi et al. (1991) Gene 103:61-67), *Geotricum candidum* lipase (See, Schimada et al. (1989) *J. Biochem.* 106:383-388), and various Rhizopus lipases such as *R. delemar* lipase (Hass et al. (1991) *Gene* 109:117-113), a *R. niveus* lipase (Kugimiya et al. (1992) *Biosci. Biotech. Biochem.* 56:716-719) and *R. oryzae* lipase. Additional lipases are the cutinase derived from *Pseudomonas mendocina* (See, WO 88/09367), and the cutinase derived from *Fusarium solani pisi* (WO 90/09446). Various lipases are described in WO 11/111143, WO 10/065455, WO 11/084412, WO 10/107560, WO 11/084417, WO 11/084599, WO 11/150157, and WO 13/033318. In some embodiments, the lipase is one or more of M1 LIPASE™, LUMA FAST™, and LIPOMAX™ (DuPont Industrial Biosciences); LIPEX®, LIPOLASE® and LIPOLASE® ULTRA (Novozymes); and LIPASE P™ "Amano" (Amano Pharmaceutical Co. Ltd., Japan).

Amylases include, but are not limited to those of bacterial or fungal origin, or even mammalian origin. Numerous suitable are described in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, WO2010115021, WO2013184577, WO9418314, WO2008112459, WO2013063460, WO10115028, WO2009061380, WO2009100102, WO2014099523, WO2015077126A1, WO2013184577, WO2014164777, PCT/US12/70334, PCT/US13/74282, PCT/CN2013/077294, PCT/CN2013/077134, PCT/CN2013/077137, PCT/CN2013/077142, PCT/CN2012/087135, PCT/US12/62209, PCT/CN2013/084808, PCT/CN2013/084809, and PCT/US14/23458. Commercially available amylases include, but are not limited to one or more of DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P, PREFERENZ® S100, PREFERENZ® S110, and PREFERENZ® S1000 (DuPont Industrial Biosciences).

Cellulases include but are not limited to those having color care benefits (see e.g., EP 0 495 257). Examples include *Humicola insolens* cellulases (See e.g., U.S. Pat. No. 4,435,307) and commercially available cellulases such as CELLUZYME®, CAREZYME® (Novozymes), and KAC-500(B)™ (Kao Corporation), and Primafast® GOLD (DuPont). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449,318, and 7,833,773.

Mannanases are described in U.S. Pat. Nos. 6,566,114, 6,602,842, 5, 476, and 775, 6,440,991, and U.S. patent application Ser. No. 61/739,267, all of which are incorporated herein by reference). Commercially available include, but are not limited to MANNASTAR®, PURABRITE®, and MANNAWAY®.

In some embodiments, peroxidases are used in combination with hydrogen peroxide or a source thereof (e.g., a percarbonate, perborate or persulfate) in the compositions of the present teachings. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments.

Perhydrolases include the enzyme from *Mycobacterium smegmatis*. This enzyme, its enzymatic properties, its structure, and numerous variants and homologs, thereof, are described in detail in International Patent Application Publications WO 05/056782A and WO 08/063400A, and U.S. Patent Publications US2008145353 and US2007167344, which are incorporated by reference.

In some embodiments, the *Mycobacterium smegmatis* perhydrolase, or homolog, includes the S54V substitution.

Other perhydrolases include members of the carbohydrate family esterase family 7 (CE-7 family) described in, e.g., WO2007/070609 and U.S. Patent Application Publication Nos. 2008/0176299, 2008/176783, and 2009/0005590. Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.,* 330:593-606 (2003)).

Other perhydrolase enzymes include those from *Sinorhizobium meliloti, Mesorhizobium loti, Moraxella bovis, Agrobacterium tumefaciens*, or *Prosthecobacter dejongeii* (WO2005056782), *Pseudomonas mendocina* (U.S. Pat. No. 5,389,536), or *Pseudomonas putida* (U.S. Pat. Nos. 5,030,240 and 5,108,457).

V. Preparation of TRWMP

The encapsulation process requires first providing the enzyme in a substantially dry form as a powder. For example, the enzyme can be spray dried from an aqueous solution or suspension, or isolated as a precipitate by addition of salts, organic solvents, or polymers to the enzyme solution. If the resulting powder precipitate contains water, it should be further dried so as to reduce the water content or water activity. The residual water content of enzyme powder, including free and bound water, should be less than 6%, preferably less than 5%, and more preferably less than 4%. The water activity (Aw) of the said enzyme powder should be less than 0.3, preferably less than 0.2, and more preferably less than 0.1.

The spray dried enzyme powder or precipitate can be further processed by dry or wet granulation such as agglomeration, compaction, or blending with other dry materials, including non-enzyme inactive excipients. In some embodiments, the enzyme solution may comprise a mixture of enzyme concentrate and optionally added excipients. The mixture may be further processed or granulated by processes such as spray agglomeration, spray granulation, low- or high-shear granulation, drum granulation and the like.

The dry enzyme, alone or further mixed, processed or granulated as described above, is then encapsulated within a porous wax matrix, which is described in detail, herein, along with optional water-soluble or water insoluble fillers, pore formers, buffers, stabilizers, swellants, disintegrants or other excipients. As described, the wax in the matrix should be water-insoluble, preferably have an onset melting point of at least 110° C. and a peak maximum melting point of at least 120° C., and preferably, have a low melt viscosity, i.e., less than about 500 centipoises at temperatures within 25° C. above its melting point.

Fillers in the wax matrix can include inorganic salts such as sodium sulfate or calcium carbonate, organic acids or salts thereof, clays, minerals such as aluminosilicates, diatomaceous earth, talc, pigments such as titanium dioxide, mono- or di-saccharides such as fructose, galactose, and glucose or lactose, maltose, sucrose and trehalose, sugar alcohols such as sorbitol or glycerol, cyclodextrins, and polysaccharides such as starch and maltodextrin or cellulose powder or gums such as xanthan gum or sodium alginate.

In some embodiments, the wax matrix includes optional water-soluble or water insoluble fillers, pore formers, buffers, stabilizers, swellants, disintegrants, degradation enhancing additives, or other excipients. The said degradation enhancing additives can promote wax degradation through different pathways including photodegradation, thermodegradation, oxo-biodegradation, biodegradation via biofilm formation, or a combination thereof. Examples of oxo-biodegradation additive technology are ADDIFLEX® (Add-X Biotech AB, Höganas, Sweden), D2W® (Symphony Environmental USA, Jacksonville, FL, USA), and TDPA®, Totally Degradable Plastic Additives (EPI Environmental Technologies Inc., Vancouver, BC, Canada). An example of biodegradation additive technology based on biofilm formation is MASTERBATCH PELLETS™ (ECM Biofilms Inc., Painesville, OH, USA).

To encapsulate the enzyme in the wax matrix, the wax must first be heated until melted. The enzyme powder is dispersed, along with any other excipients, within the molten wax. The enzyme can be added before, after, or simultaneously with any excipients. The solid-liquid dispersion can be carried out batch-wise or fed-batch in a stirred tank vessel, or continuously in an inline mixer. Once the enzyme is adequately dispersed to form a suspension in the molten wax, the wax suspension is atomized into particles. For example, a stream of the molten suspension can be extruded or pumped onto a spinning disk atomizer. Microcapsule particle formation by spinning disk atomization is described in e.g., U.S. Pat. Nos. 3,015,128, 4,256,677 and 6,001,387. Alternatively, the wax microcapsules can be formed by other atomization methods such a centrifugal extrusion (see, e.g., U.S. Pat. No. 4,386,895), vibratory nozzle atomization (see, e.g., WO2012/098239) or jet cutting (see, e.g., DE 4,424, 998 and U.S. Pat. No. 6,467,699. ), followed by cooling to solidify the particles and collecting the solidified particles.

In spinning disk atomization, the mean particle size and particle size distribution of the final particles can be controlled by adjusting the rotational velocity of the atomizing disk, in consideration of the disk diameter, the flow rate of the suspension and the viscosity and surface tension of the molten suspension. For a given disk apparatus, particle size is reduced by increasing the rotational velocity of the disk, reducing the feed rate of molten suspension, and/or reducing the viscosity and surface tension of the molten suspension.

In order to produce smaller well-formed microparticles it is preferred to use a molten suspension with a low melt viscosity. For example, to produce microparticles of less than 500 microns, it is desirable to use a wax with a melt viscosity of less than 500 centipoises at temperatures within 25° C. above the wax melting temperature.

VI. Properties of TRWMP

The resulting TRWMP are coating-free, substantially-spherical, microgranules, that are smaller than about 500 microns in average diameter, and contain active enzymes at payloads greater than 5% w/w. The particular properties of the wax matrix are described in detail, herein.

In some embodiments, the encapsulated enzymes retain at least 70%, preferably at least 80%, and more preferably at least 90%, or more of the original enzyme activity upon exposure to a temperature 95° C. for 30 seconds in a typical animal feed pelleting process. Activity retention is easily measured by comparing the activity of enzymes that went into granule production with the amount of activity in the final TRWMP. These and other aspects and embodiments of the present compositions and methods will be apparent to the skilled person in view of the present description. The following examples are intended to further illustrate, but not limit, the compositions and methods.

EXAMPLES

Example 1. Thermal Analysis of Polymeric and Non-Polymeric Waxes

Thermal analysis of commercial Fischer-Tropsch waxes, polyethylene waxes, zinc stearates, and stearic acid were carried out by differential scanning calorimetry (DSC) on a TA Instruments DSC Q2000 thermal analyzer in nitrogen atmosphere.

Samples of F-T and PE waxes were heated from 20° C. to 180° C. at a heating rate of 10° C. $min^{-1}$ and cooled to 20° C. at the same rate in the first scan. They were then heated to 180° C. at a heating rate of 2° C. $min^{-1}$ and cooled to 20° C. at the same rate in the second scan. Samples of zinc stearates and stearic acid were heated from 20° C. to 160° C. at a heating rate of 10° C. $min^{-1}$ and cooled to 20° C. at the same rate in the first scan. They were then heated to 160° C. at a heating rate of 5° C. $min^{-1}$ and cooled to 20° C. at the same rate in the second scan. Thermal properties such as melting onset point, maximum peak and the area under heat flow curve (W/g vs. ° C.) were determined from the heating cycle of the second scan. The area under the heat flow curve (AUC) is proportional to the total enthalpy change of the sample for the heating process between the initial and final temperatures of the DSC scan. The variation of enthalpy-change with time (t), temperature (T), or scanning rate (dT/dt) depends on the degree of molecular mass uniformity of waxes.

DSC thermograms including the melting onset point, maximum peak, and enthalpy change ratio between 40° C. and 140° C. ($ECR_{(40,140)}$) are shown in FIGS. 1-5. Waxes suitable for the present compositions and methods are those with an $ECR_{(40,140)}$ of less than 20%, preferably less than 15%, and more preferably less than 10%. The preferred waxes have a melting onset point and maximum peak point of respectively above 100° C. and 120° C.

Example 2. Preparation of Enzyme Powder with Spray Drying

This Example provides a general description of materials and methods used for production of enzyme powder with spray drying process. Spray dried enzyme powder was produced by spray drying an enzyme solution (or concentrate) in a Niro P-6.3 spray dryer (GEA Process Engineering A/S, Søborg, Denmark) equipped with a rotary atomizer configured in a co-current mode. The enzyme solution (or concentrate) was fed into the spray dryer using a Watson-Marlon peristaltic pump, model 505U (Watson-Marlow Pumps Group, Wilmington, MA, USA) and subsequently atomized by high speed rotary atomizer. The rotary atomizer was placed in the ceiling air disperser and operated with the vaned atomizer wheel (12 cm dia) rotating at 14,000 rpm. The spray dryer was thermally equilibrated with cooling de-mineralized water at about 10-15° C. before spraying. Typical process conditions are summarized in Table 2. Spray dried enzyme powder was collected at the end of each run and stored in sealed double plastic bags at room temperature.

TABLE 2

Typical spray drying process conditions for production of enzyme powder

| | | |
|---|---|---|
| Enzyme concentrate | Temperature | 5-15° C. |
| | Stirring Time | 10-30 min |
| | Feed Rate | 10-30 kg/h |
| Process air | Inlet Temperature | 160-200° C. |
| | Outlet Temperature | 75-110° C. |
| | Flow Rate | 500-600 $m^3/h$ |

Particle size distribution of enzyme powder was analyzed by the laser diffraction method. The characteristic particle sizes of $d_{10}$, $d_{50}$ (median) and $d_{90}$, corresponding respectively to 10%, 50%, and 90% points on the cumulative volume-size distribution curve, lied within a narrow range. For phytase powder samples listed in the following Examples 4-7, $d_{10}$ ranged from 11-14 μm, $d_{50}$ from 25-39 μm, and $d_{90}$ ranged from 53-105 μm.

Figure 6:
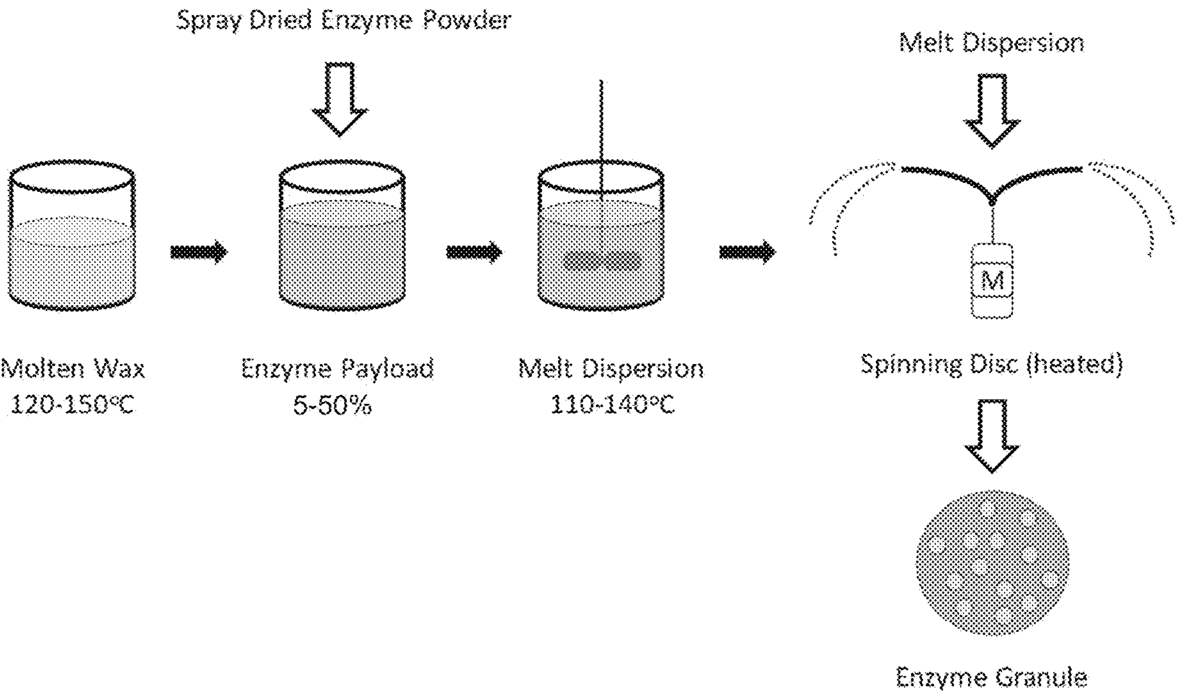
FIG. 6 is a schematic diagram of a spinning disk atomization setup used for production of enzyme granules. Enzyme payload and temperature values shown are exemplary.

Example 3. Production of Enzyme Granules with Hot-Melt Spinning Disk Atomization Enzyme granules to be described in the following Examples were produced by using a spinning disk atomizer in a laboratory setup as illustrated in FIG. 6. A wax substance (meltable carrier) was first heated to melt in a glass container. The molten wax was further heated and maintained at 15-30° C. above the melting point. Inactive ingredients and then active spray dried enzyme powder, produced as described in Example 2 were dispersed in the molten wax while being stirred manually. Inactive ingredients were selected from fillers, binders, stabilizers, disintegrants, surfactants, osmolality agents, pH modifying agents, and mixtures thereof. A list of exemplary inactive excipients, their manufacturer/supplier and melting point used in the exemplified compositions, is provided in Table 3.

TABLE 3

List of exemplary inactive excipients

| Material | Manufacturer/ Supplier | Onset m.p. (° C.) | Peak max. m.p. (° C.) | $ECR_{(40, 140)}$ | Melt viscosity (cP) |
|---|---|---|---|---|---|
| Calcium carbonate, MICROWHITE ® 30 Codex | Imerys Performance Minerals | — | — | — | — |
| Calcium carbonate GLC-1012 | Great Lakes Calcium | — | — | — | — |
| PICCOLYTE ® C125 | Pinova | — | 127 | — | — |
| PICCOLYTE ® A135 Plus | Pinova | — | 133 | — | — |
| Calcium stearate | Alfa Aesar | — | 153 | — | — |
| Sodium stearate | Sigma-Aldrich | — | 250 | — | — |
| Stearic acid | Sigma-Aldrich | 69.6 | 73.1 | 99.69% | — |
| Microcrystalline wax 863 | Frank B. Ross | — | 95 | — | — |
| Sasolwax C105 | Sasol Wax North America | 88.0 | 101.1 | 45.94% | 13 @ 135° C. |
| Honeywell A-C ® 820A | Honeywell | 120.0 | 124.3 | 15.26% | 86 @ 140° C. |
| ZINCUM ® SMS Veg, Zinc Stearate | Baerlocher | 120.2 | 123.1 | 13.17% | — |
| ZINCUM ® SP VEG Prills, zinc stearate | Baerlocher | 120.2 | 123.5 | 9.68% | — |
| POLYWAX ™ 2000 | Baker Hughes | 120.6 | 124.7 | 6.07% | 51 @ 149° C. |

The melt dispersions were homogenized by using a high shear homogenizer to ensure that a consistent lump-free dispersion was attained. The melt dispersions were then dispensed manually, or using a peristaltic pump, at a steady rate, onto a heated spinning stainless-steel disk (10 cm diameter) for atomization. The disk was installed at about 4.6 meters above the floor and operated at about 1500 to 6500 rpm using a hydraulic pressure pump. Fine melt droplets formed by atomization were solidified into particles at room temperature. The particles were collected manually and kept in sealed plastic containers at room temperature.

The overall melt processing time was less than 2.5-5 min, including mixing the materials and feeding the spinning disk. The atomization of melt formulations was taken place in a confined chamber of about 80 cubic meters at normal ambient room conditions.

Example 4. Production of Phytase Granules Composed of Spray Dried Enzyme Powder and Low-Melting Wax as Matrix Material with Hot-Melt Spinning Disk Atomization The following is a comparative example of enzyme formulations made using low melting carriers that do not satisfy pelleting stability requirements as described in Example 10.

Phytase granule formulations were produced with spinning disk atomization method described in Example 3. Hot melt compositions were prepared by adding spray dried phytase powder, prepared as described in Example 1, and calcium carbonate to the molten wax. Processing time was approximately 5 min including mixing the materials and dispensing the melt preparation onto the spinning disk. Fine melt droplets formed by atomization were rapidly solidified into particles at room temperature. The particles were collected and stored in sealed plastic containers. The composition of phytase granule formulations is provided in Table 4. Melt compositions containing calcium stearate and sodium stearate were prepared at 90-110° C. as the stearate salts were soluble in the molten stearic acid.

TABLE 4

Composition (% w/w) of phytase and low-melting wax granules produced with hot-melt spinning disk atomization

| Ingredient | P2 | P4 | P44 | P46 | P54 |
|---|---|---|---|---|---|
| Phytase powder | 10% | 10% | 10% | 10% | 10% |
| Calcium carbonate, MICROWHITE ® 30 Codex | 10% | 40% | — | — | 40% |
| Stearic acid | 80% | 50% | 60% | 60% | — |
| Sodium stearate | — | — | 30% | 10% | — |
| Calcium stearate | — | — | — | 20% | — |
| Microcrystalline wax 863 | — | — | — | — | 50% |
| Total | 100% | 100% | 100% | 100% | 100% |
| Batch size | 500 g | 500 g | 250 g | 250 g | 250 g |

Example 5. Production of Phytase Granules Composed of Spray Dried Enzyme Powder and High-Melting Wax as Matrix Material with Hot-Melt Spinning Disk Atomization The following is an example of enzyme formulations with high melting carrier that, depending on their ECR values, satisfy pelleting stability requirement as described in Example 11.

Phytase granule formulations were produced with spinning disk atomization method described in Example 3. Hot melt compositions were prepared by adding spray dried phytase powder, prepared as described in Example 1, and calcium carbonate to the molten wax at about 152° C. Processing time was less than 2.5 min including mixing the materials and dispensing the melt preparation onto the spinning disk. Fine melt droplets formed by atomization were rapidly solidified into particles at room temperature. The particles were collected and stored in sealed plastic containers. The composition of phytase granule formulations is provided in Table 5.

TABLE 5

Composition (% w/w) of phytase and high-melting wax granules produced with hot-melt spinning disk atomization

| Ingredient | P40.4 | P58.1 | P96.1 | 97.6 | P97.2 |
|---|---|---|---|---|---|
| Phytase powder | 10% | 10% | 20% | 20% | 20% |
| Calcium carbonate GLC-1012 | — | — | 10% | 10% | 20% |
| Sasolwax C105 | 90% | — | — | — | — |
| Honeywell A-C ® 820A | — | 90% | — | — | — |
| POLYWAX ™ 2000 | — | — | 70% | 70% | 60% |
| Total | 100% | 100% | 100% | 100% | 100% |
| Batch size | 180 g | 500 g | 400 g | 500 g | 400 g |

Example 6. Production of Phytase Granules Composed of Spray Dried Enzyme Powder and (Low-Melting) Stearic Acid and (High-Melting) Zinc Stearate as Matrix Materials with Hot-Melt Spinning Disk Atomization The following is a comparative example of enzyme formulations as described in Example 5 of International Patent Application WO03056934A2 (assigned to Cargill), entitled, encapsulation by coating with a mixture of lipids and hydrophobic, high melting point compounds," demonstrating that these earlier formulations do not satisfy the present pelleting stability.

Phytase granule formulations were produced with spinning disk atomization method described in Example 3. Stearic acid (m.p. 73° C.) and ZINCUM® SMS Veg zinc stearate (m.p. 121° C.) were used as matrix materials. Hot melt compositions were prepared by adding the spray dried phytase powder to the molten wax preparation at about 152° C., wherein stearic acid/zinc stearate ratio was 9:1 on a weight per weight basis. The melt preparation was transferred manually and steadily as a single stream onto the spinning disk. Processing time was approximately 1.3 min including mixing the materials and feeding the spinning disk. Fine melt droplets formed by atomization were rapidly solidified into particles at room temperature. The particles were collected and stored in sealed plastic containers. The composition of phytase granule formulations is provided in Table 6.

TABLE 6

Composition (% w/w) of phytase granules produced with hot-melt spinning disk atomization

| Ingredient | P166.4 |
|---|---|
| Stearic acid | 72% |
| ZINCUM ® SMS Veg | 8% |
| Phytase, spray dried powder | 20% |
| Batch size | 400 g |

Example 7. Production of Phytase Granules Composed of Spray Dried Enzyme Powder and Zinc Stearate and Polyterpene Resin as High-Melting Matrix Materials with Hot-Melt Spinning Disk Atomization Phytase granule formulations were produced with spinning disk atomization method described in Example 3. ZINCUM® SP VEG zinc stearate (m.p. 121° C.), PICCOLYTE® C125 (softening point 125° C.), and PICCOLYTE® A135 Plus (softening point 135° C.) were used as matrix materials. Hot melt compositions were prepared by adding the spray dried phytase powder to the molten wax preparation at about 152° C. The melt preparation was transferred manually and steadily as a single stream onto the spinning disk. Processing time was approximately 1-1.5 min including mixing the materials and feeding the spinning disk. Fine melt droplets formed by atomization were rapidly solidified into particles at room temperature. The particles were collected and stored in sealed plastic containers. The composition of phytase granule formulations is provided in Table 7.

TABLE 7

Composition (% w/w) of phytase granules produced with hot-melt spinning disk atomization

| Ingredient | P166.1 | P170.2 | P171.3 |
|---|---|---|---|
| ZINCUM ® SP VEG | 60% | 48% | 48% |
| PICCOLYTE ® C125 | — | 12% | — |
| PICCOLYTE ® A135 Plus | — | — | 12% |
| Calcium carbonate | 20% | 20% | 20% |

TABLE 7-continued

| Composition (% w/w) of phytase granules produced with hot-melt spinning disk atomization | | | |
|---|---|---|---|
| Ingredient | P166.1 | P170.2 | P171.3 |
| Phytase, spray dried powder | 20% | 20% | 20% |
| Batch size | 400 g | 400 g | 400 g |

Example 8. Procedures for Steam Conditioning of Animal Feed Containing Enzyme Granules Thermal stability of enzyme granules was evaluated in a miniature feed milling plant with a nominal pelletizing capacity of 300 kg/h. Conditioning was performed under different controlled temperatures, e.g., 90 and 95° C. Production of the feed mixture, mixing technique, resting time, capacity, and cooling time were identical for all formulations. Only the addition of enzymes and the addition of steam in the cascade mixer to reach the desired conditioning temperature varied.

The feed mill consisted of a horizontal mixer with a volume capacity of 700 L and a mixing capacity of 80-300 kg, running at a speed of 48 rpm; a dosing screw of the type Skjold TR with adjustable speed (used for emptying the mixer and for dosing the feed); a cascade mixer of the type KAHL, 130 cm×30 cm×length×diameter, with 37 adjustable pallets operating at a speed of 155 rpm (dwell time in the cascade mixer was approximately 30 seconds estimated based on a production rate of 300 kg/h); a collection manifold mounted on one side of the cascade mixer with a water discharger and 3 steam valves from which steam was added to the feed; and a high-pressure boiler of the type Dan Stroker with a maximum capacity of 400 kg steam/h.

The steam was added to the feed with an expansion valve controlling the addition of steam to the cascade mixer. The three valves on the collection manifold were used for fine-tuning the desired temperature in the feed. The temperature of the feed increased by 14° C. for 1% steam added. The temperature of the meal was recorded with a digital thermometer of the type Testo 925 with a Pt 100 sensor. The sensor was placed by the mouth of the cascade mixer. The thermometer was calibrated with an approved mercury thermometer of the type Goldbrand/39 Q9732-818.

The pellet press used was a Simon Heesen of the type Labor Monoroll with a 7.5 kW motor. The internal diameter of the matrix was 173 mm with a 3 mm×35 mm (hole diameter×channel length) die. The height and diameter of press were 50 mm and 140 mm, respectively. The samples were cooled in a partitioned cooling box with perforated bottom through which the meal feed was cooled by a ventilator with a capacity of 1500 $m^3$ air/h.

The formulation of feed mixture corresponded to a regular standard corn diet as shown in Table 17. A sufficient quantity of the feed mixture was prepared in each trial. This basic mixture was produced in one lot in a mill and mixing installation, and stored in a container before each trial. A feed 'premix' was prepared by blending a given amount of enzyme granules with 10 kg of the feed mixture in a 70 L compulsory mixer operating at 45 rpm for 10 min. The premix was then added to about 110 kg of the feed mixture in the horizontal mixer of the feed mill and mixed for 10 minutes to produce the 'trial feed' or 'mash'. In case of phytase, adequate amount of phytase granules were added to the premix to yield a target enzyme activity of 5,000 FTU/kg trial feed. A 'pre-steam' sample was collected from the trial feed before pelletizing and stored in a labeled container at normal ambient temperature until analysis for enzyme activity.

A reference phytase granule product (served as control) with known phytase activity was added at 5,000 FTU/kg trial feed in all pelleting trials as control.

TABLE 8

| Composition of standard corn diet in pelleting trials | |
|---|---|
| Ingredient | Weight Percent |
| Corn | 61.10% |
| Soybean meal 48 | 31.43% |
| Soy oil | 4.00% |
| Salt | 0.40% |
| DL-Methionine | 0.20% |
| Limestone | 1.16% |
| Dicalcium phosphate | 1.46% |
| Vitamins/minerals premix | 0.25% |
| Total | 100.00% |

The trial feed was pelletized in the Simon Heesen pellet press with the die. The capacity was set to 300 kg/h and was adjusted to the dosing screw. The feed was heated to the target outlet (or discharge) temperatures of 90 and 95° C. by steam in the cascade mixer. The steam quantity was regulated by the pressure reduction valve and the manifold. The 'post-steam' sample was collected as sub-samples of approximately 0.5 kg which were immediately removed 10-15 seconds after the pellets have left the pellet press and placed in a cooling box. For each temperature level the first sub-sample was taken when operation was established after 8-10 min pelletizing. Sub-samples were collected during a period of 1-1.5 min, corresponding to 5-7.5 kg of pelletized feed. All samples were aerated and cooled at ambient temperature for 15 minutes, which ensured the removal of surplus heat from the pellets. The post-steam sample was stored in a labeled container at normal ambient temperature until analysis for enzyme activity.

Prior to the production of the meal mixture in the mill and mixing installation, the feed mill was cleaned of feed remnants and the mixer was vacuum-cleaned. The miniature feed mill was cleaned before and after each trial. Mixer and dosing equipment were vacuum-cleaned, and the cascade mixer was self-emptying. The small mixer for premix and the cooling box were cleaned thoroughly after each trial.

Example 9. Analysis of Phytase Activity of Feed Samples

An in-house method of analysis was developed in order to accurately analyze the activity of *T. reesei* phytase in animal feeding stuffs and in premixes containing phytase granules when mixed into feed. The method is very similar to the harmonized standard method ISO 30024:2009 (i.e., ISO 30024: Animal feeding stuffs—Determination of Phytase Activity, 2009) and follows the same principle, i.e. the phytase is incubated with sodium phytate, which results in the release of inorganic phosphate. The inorganic phosphate creates a yellow colored complex when reacted with molybdate-vanadate reagent. The optical density of the yellow complex is measured at a wavelength of 415 nm. The extent of color formation can be directly related to the enzyme activity. Quantification of activity is made by an absolute method using a phosphate standard calibration curve.

This method was developed according to the principles set out in ISO 9001 (i.e., ISO 9001: 2008 Quality Management Systems) and Good Laboratory Practice and has been written in accordance with the rules given in ISO 78-2:1999 (i.e., ISO 78-2: Chemistry—Layouts for standards—Part 2: Methods of Chemical Analysis, 1999).

A phytase Unit of Activity (FTU) was defined as the amount of enzyme that releases 1 μmol of inorganic orthophosphate from a sodium phytate substrate per minute at pH 5.5 and 37° C. Milled feed samples with known phytase activity (5,000 FTU/kg) were used as a control.

Example 10. Thermal Stability of Granulated Phytase to Steam Conditioning of Animal Feed Containing Phytase Granules Made of Low-Melting Wax as Matrix Material The following is a comparative example illustrating that the enzyme formulations with low melting carriers described in Example 4 do not satisfy the present pelleting stability requirements.

Phytase granules of Example 4 were evaluated in animal feed pelleting trials in accordance with the procedures described in Examples 8 and 9. The particle size range of test formulations is shown in Table 9.

TABLE 9

Particle size distribution (% w/w) of phytase granule formulations evaluated in pelleting trial

| Formulation | Particle Size Range |
|---|---|
| P2 | 212-300 μm |
| P4 | 212-300 μm |
| P44 | 212-300 μm |
| P46 | 212-300 μm |
| P54 | 212-300 μm |

The enzyme activity of phytase granule formulations measured in the feed mash before, and the relative residual activity after processing with steam are shown in Table 10. All the phytase formulations made with low-melting wax as matrix material lost at least 85% of their initial enzyme activity in the steam pelleting process (n=2, avg±std dev).

TABLE 10

Enzyme activity of phytase granules produced with hot-melt spinning disk atomization

| Formulation | Initial activity (FTU/g) | Relative residual activity (%) 90° C. | Relative residual activity (%) 95° C. |
|---|---|---|---|
| P2 | 30160 ± 1450 | 8.1% ± 1.8% | 4.8% ± 1.7% |
| P4 | 32084 ± 1040 | 6.8% ± 1.0% | 5.2% ± 0.5% |
| P44 | 20234 ± 558 | 14.8% ± 2.4% | 5.1% ± 2.9% |
| P46 | 19608 ± 1038 | 7.7% ± 0.8% | 6.5% ± 1.0% |
| P54 | 12990 ± 1810 | 8.4% ± 2.2% | 7.8% ± 2.1% |

Example 11. Thermal Stability of Granulated Phytase to Steam Conditioning of Animal Feed Containing Phytase Granules Made of High-Melting Wax as Matrix Material The following is an example illustrating the enzyme formulations with the high melting carriers described in Example 5, which satisfy the present pelleting stability requirements. Phytase granules of Example 5 were evaluated in animal feed pelleting trials in accordance with the procedures described in Examples 9 and 10. The particle size range of test formulations is shown in Table 11.

TABLE 11

Particle size range (% wt/wt) of phytase granule formulations evaluated in pelleting trial

| Formulation | Particle Size Range |
|---|---|
| P40.4 | 212-425 μm |
| P58.1 | 212-300 μm |
| P96.1 | 212-300 μm |
| P97.6 | 212-300 μm |
| P97.2 | 212-300 μm |

The enzyme activity of phytase granule formulations measured in the feed mash before, and the relative residual activity after processing with steam are shown in Table 12. All of phytase formulations made with high-melting wax as matrix material retained at least 50% of their initial enzyme activity in the steam pelleting process. The preferred compositions, made with a high-melting wax with an $ECR_{(40,140)}$ of 6.1%, maintained at least 85% of their initial activity after pelleting at 95° C. (n=2, avg±std dev).

TABLE 12

Enzyme activity of phytase granules produced with hot-melt spinning disk atomization

| Formulation | Initial activity (FTU/g) | Relative residual activity (%) 90° C. | Relative residual activity (%) 95° C. |
|---|---|---|---|
| P40.4 | 10979 ± 98 | 54.7% ± 5.2% | 51.3% ± 9.4% |
| P58.1 | 17800 ± 148 | 74.4% ± 1.1% | 68.8% ± 5.4% |
| P96.1 | 29852 ± 2176 | 89.5% ± 8.4% | 86.1% ± 6.6% |
| P97.6 | 21604 ± 704 | 102.4% ± 16.8% | 84.9% ± 3.6% |
| P97.2 | 31744 ± 4032 | 96.4% ± 24.3% | 100.2% ± 14.6% |

Example 12. Thermal Stability of Granulated Phytase to Steam Conditioning of Animal Feed Containing Phytase Granules Made of Stearic Acid and Zinc Stearate, Zinc Stearate, and Zinc Stearate and Polyterpene Resins The following is an example illustrating the performance of the phytase granules of Examples 6 and 7 as evaluated in animal feed pelleting trials in accordance with the procedures described in Examples 8 and 9. The particle size range of test formulations is shown in Table 13.

TABLE 13

Particle size distribution (% wt/wt) of phytase granule formulations evaluated in pelleting trial

| Formulation | Particle Size Range Sample 1 | Particle Size Range Sample 2 |
|---|---|---|
| P166.1 | 212-300 μm | 300-425 μm |
| P166.4 | 212-425 μm | — |
| P170.2 | 212-300 μm | 300-425 μm |
| P171.3 | 212-300 μm | 300-425 μm |

The enzyme activity of phytase granule formulations measured in the feed mash before, and the relative residual activity after processing with steam are show in Table 14. The phytase formulation P166.4 (as described in WO03056934A2) containing low-melting stearic acid lost all of its initial enzyme activity during the pelleting process. The phytase formulations P170.2 and P171.3 made with high-melting zinc stearate and a PICCOLYTE® resin showed improved pelleting stability compared to the formulation P166.1 that was made with zinc stearate alone as a matrix material (n=2, avg±std dev).

TABLE 14

Enzyme activity of phytase granules produced with hot-melt spinning disk atomization

| Formu-lation | Initial enzyme activity (FTU/g) Sample 1 | Initial enzyme activity (FTU/g) Sample 2 | Relative residual Activity (%) Sample 1 90°C. | Sample 1 95°C. | Sample 2 90°C. | Sample 2 95°C. |
|---|---|---|---|---|---|---|
| P166.4 | 51878 | — | 0% | 0% | — | — |
| P166.1 | 40696 ± 2254 | 43583 ± 6949 | 73.1% ± 4.3% | 41.1% ± 4.6% | 69.1% ± 11.9% | 48.8% ± 8.3% |
| P170.2 | 39502 ± 1740 | 44954 ± 2524 | 86.3% ± 5.7% | 71.9% ± 3.4% | 77.6% ± 4.7% | 75.0% ± 4.2% |
| P171.3 | 41851 ± 3694 | 44320 ± 305 | 81.6% ± 19.6% | 58.5% ± 6.5% | 79.6% ± 7.9% | 77.1% ± 3.1% |

Examples 13 and 14 describe bioavailability studies performed on broiler chicks and pigs to evaluate the bioefficacy of present phytase granule formulations in comparison with a commercial product.

Example 13: Bioefficacy of Polyethylene Wax-Microencapsulated Phytase Granules in Broiler Chicks Three separate in vivo studies ("A", "B" and "C") were conducted to evaluate and compare the bioefficacy of phytase granule formulations, produced with hot-melt spinning disk atomization as described in Example 3. Three formulations P75.1M and P75.4M, P96.5 consisted of spray dried phytase microencapsulated in a polyethylene (PE) homopolymer wax, POLYWAX™ 2000 (Table 15). The bioefficacy of PE wax-microencapsulated phytase granules was compared with that of a commercial Danisco AXTRA® PHY product (a variant phytase from a *Buttiauxella* sp.). Studies A and B involved formulations P75.1M, P75.4M, and AXTRA® PHY, and each consisted of eight treatments (Table 16). Study C involved formulations P75.1M, P96.5 and AXTRA® PHY, and consisted of eight treatments (Table 17).

TABLE 15

Composition (% w/w) of phytase granules produced with hot-melt spinning disk atomization

| Ingredient | Formulation P75.1M | P75.4M | P96.5 |
|---|---|---|---|
| Phytase powder | 20% | 20% | 20% |
| Calcium carbonate GLC-1012 | — | 10% | 20% |
| POLYWAX ™ 2000 | 80% | 70% | 60% |
| Total | 100% | 100% | 100% |
| Batch size | 400 g | 400 g | 400 g |

TABLE 16

Experimental design for studies A and B

| Dose | Dietary treatment | Dietary nPP level (%) | Phytase level (FTU/kg) |
|---|---|---|---|
| 1 | Negative control (NC) | 0.15 | 0 |
| 2 | NC + AXTRA ® PHY | 0.15 | 300 |
| 3 | NC + AXTRA ® PHY | 0.15 | 600 |
| 4 | NC + AXTRA ® PHY | 0.15 | 1000 |
| 5 | NC + P75.1M | 0.15 | 300 |
| 6 | NC + P75.1M | 0.15 | 600 |
| 7 | NC + P75.4M | 0.15 | 300 |
| 8 | NC + P75.4M | 0.15 | 600 |

TABLE 17

Experimental design for study C

| Dose | Dietary treatment | Dietary nPP level (%) | Phytase level (FTU/kg) |
|---|---|---|---|
| 1 | Negative control (NC) | 0.15 | 0 |
| 2 | NC + AXTRA ® PHY | 0.15 | 300 |
| 3 | NC + AXTRA ® PHY | 0.15 | 600 |
| 4 | NC + AXTRA ® PHY | 0.15 | 1000 |
| 5 | NC + P75.1M | 0.15 | 300 |
| 6 | NC + P75.1M | 0.15 | 600 |
| 7 | NC + P96.5 | 0.15 | 300 |
| 8 | NC + P96.5 | 0.15 | 600 |

One-day old Ross 708 male broiler chicks were used in all studies. At study initiation, 8 birds were randomly allocated to battery cages according to respective treatments by blocks. Only healthy birds were selected for the experiment, and no birds were replaced throughout the course of the study.

Bird weights were recorded at study initiation (day 0), on day 7, and at study termination (day 14). The cage was the experimental unit. Diets were fed in mash form and were formulated to meet or exceed NRC (National Research Council) standards, except for Ca and AvP (Table 18). All feed was mixed using a Davis S-20 mixer (H.C. Davis Sons Manufacturing Co., Bonner Springs, KS, USA). The mixer was flushed between each treatment to prevent cross contamination between rations. Samples were collected from each treatment diet from the beginning, middle and end of each batch and were minced together for analysis of enzyme activity in feed.

All birds were fed a corn soy base ration until day 7; from day 7 the treatment rations were fed. At the feed change, feeders were removed from the cages, weighed back, emptied, and refilled with the appropriate treatment diet. On the final day of the study, feed was weighed.

TABLE 18

Diet formulations

| Ingredient | Starter (0-7 days) inclusion (%) | NC (7-14 days) inclusion (%) |
|---|---|---|
| Maize | 52.09 | 58.27 |
| Soybean meal 48% CP | 42.53 | 37.56 |
| Pig/poultry fat | 1.32 | 1.62 |
| L-Lysine HCl | 0.12 | 0.056 |
| DL-methionine | 0.30 | 0.24 |
| L-threonine | 0.039 | 0.0025 |
| Salt | 0.32 | 0.32 |
| Limestone | 1.11 | 1.37 |
| Dicalcium phosphate | 1.68 | 0.061 |

TABLE 18-continued

| Diet formulations | | |
|---|---|---|
| Ingredient | Starter (0-7 days) inclusion (%) | NC (7-14 days) inclusion (%) |
| Poultry vit/TE | 0.5 | 0.5 |
| Met energy | 12.13 | 12.55 |
| Crude protein | 25 | 23 |
| Calcium | 1 | 0.7 |
| Non-phytate p (nPP) | 0.45 | 0.15 |
| Na | 0.16 | 0.16 |
| Cl | 0.25 | 0.24 |
| Avail Lys | 1.27 | 1.1 |
| Avail Met + Cys | 0.94 | 0.84 |
| Avail Thr | 0.83 | 0.73 |
| Avail Trp | 0.26 | 0.24 |

At study termination, six birds per cage (two birds of average weight, two birds below average weight, and two birds above average weight) were selected for bone ash measurements. The right tibia of each bird was removed. The bone was dried overnight at 100° C., divided into three equal parts, the two end parts (epiphysis) were weighed together and the middle part was weighed in a separate crucible, the bones were then ashed in a muffle furnace for 16 hours at 600° C. Ash was then expressed as a percentage based on the weight of the reaming ash as a proportion of the dry bone weight. The epiphyseal bone ash and middle bone ash were added together to enable calculation of whole tibia ash. For toe ash measurements, all birds per cage were used, taking the middle toe, separated at the third phalange distally to proximately, toes were pooled on a pen basis and ashed in separate crucibles to those with the tibiae. Data were analyzed using ANOVA, and means separation conducted to test differences between the different enzyme formulations and enzyme doses. Cage was used as the experimental unit.

Figure 7:
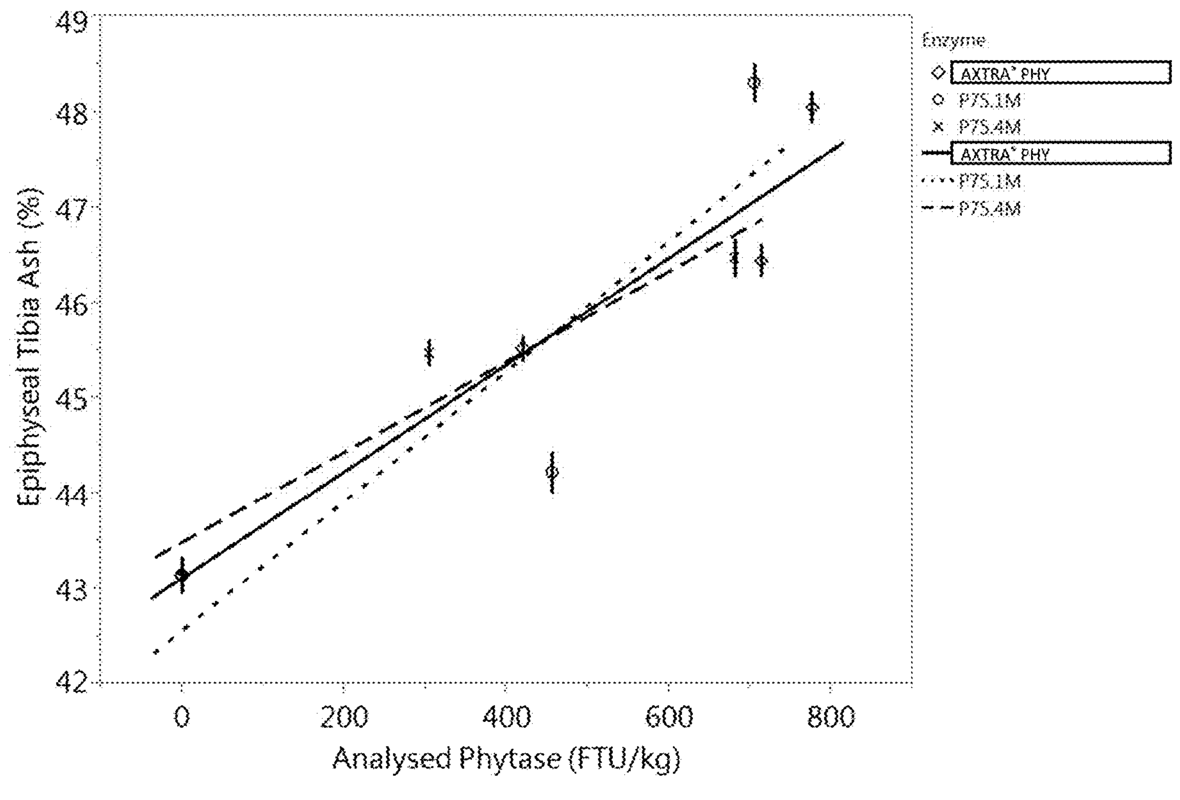
FIG. 7 is a graph showing the variation of epiphyseal tibia ash measured in a feed phytase bioefficacy study. Test phytase granules were polyethylene wax-microencapsulated-phytase granules P75.1M and P75.4M. Commercial Danisco AXTRA® PHY product granules served as a control.
Figure 8:
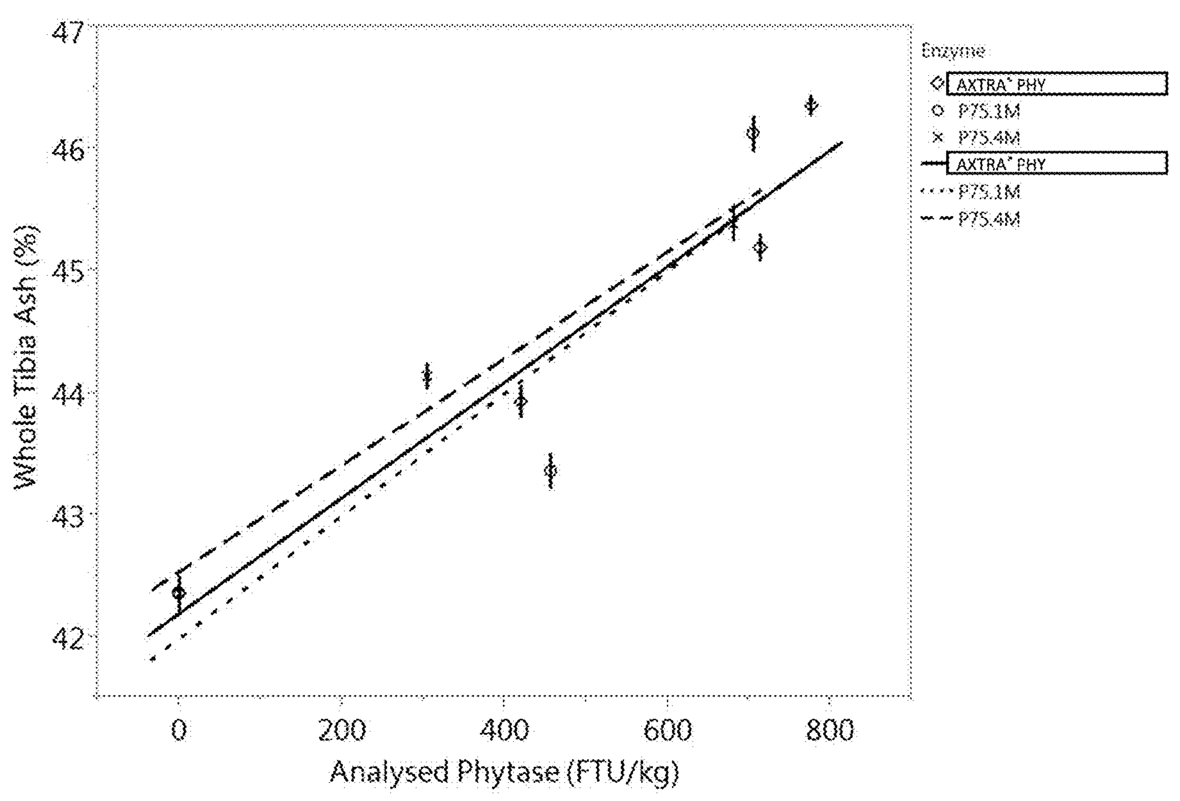
FIG. 8 is a graph showing the variation of whole tibia ash measured in a feed phytase bioefficacy study using the same granules as in FIG. 7.
Figure 9:
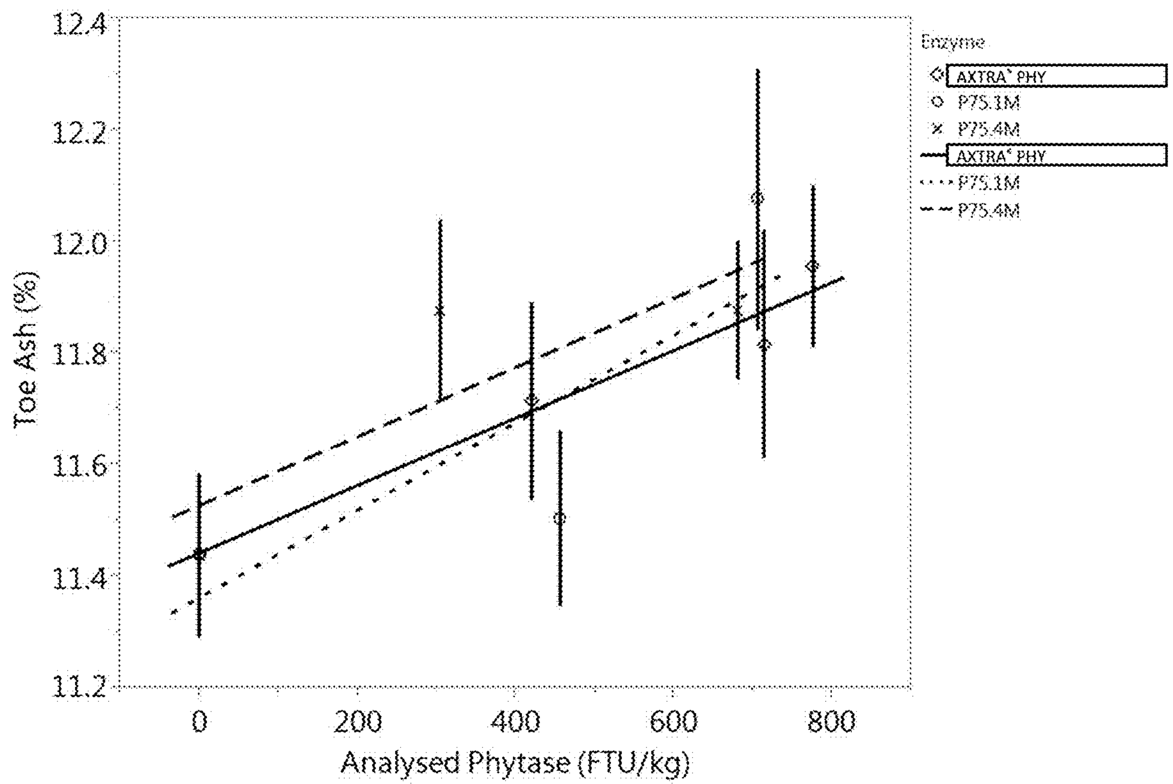
FIG. 9 is a graph showing the variation of toe ash measured in a feed phytase bioefficacy study using the same granules as in FIG. 7.

FIGS. 7-9 show, respectively, the variation of epiphyseal tibia ash, whole tibia ash, and toe ash with measured in-feed phytase activity in study A. The results obtained for the epiphyseal tibia ash, whole tibia ash, and toe ash indicated that there was no significant difference in the bioavailability of the enzyme between the formulations of this invention and the commercial AXTRA® PHY product. There was a significant effect of phytase on bone ash, whereby higher inclusion levels of enzyme resulted in higher bone ash.

Figure 10:
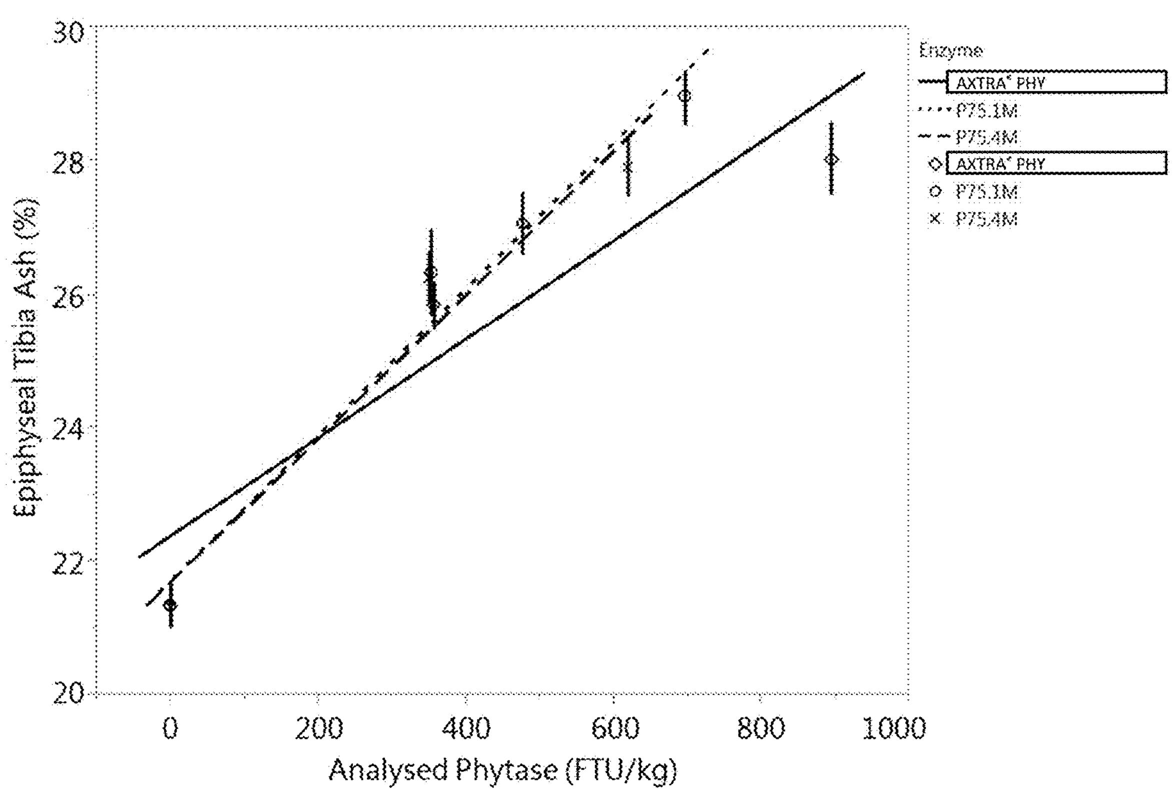
FIG. 10 is a graph showing the variation of epiphyseal tibia ash measured in a feed phytase bioefficacy study using the same granules as in FIG. 7.
Figure 11:
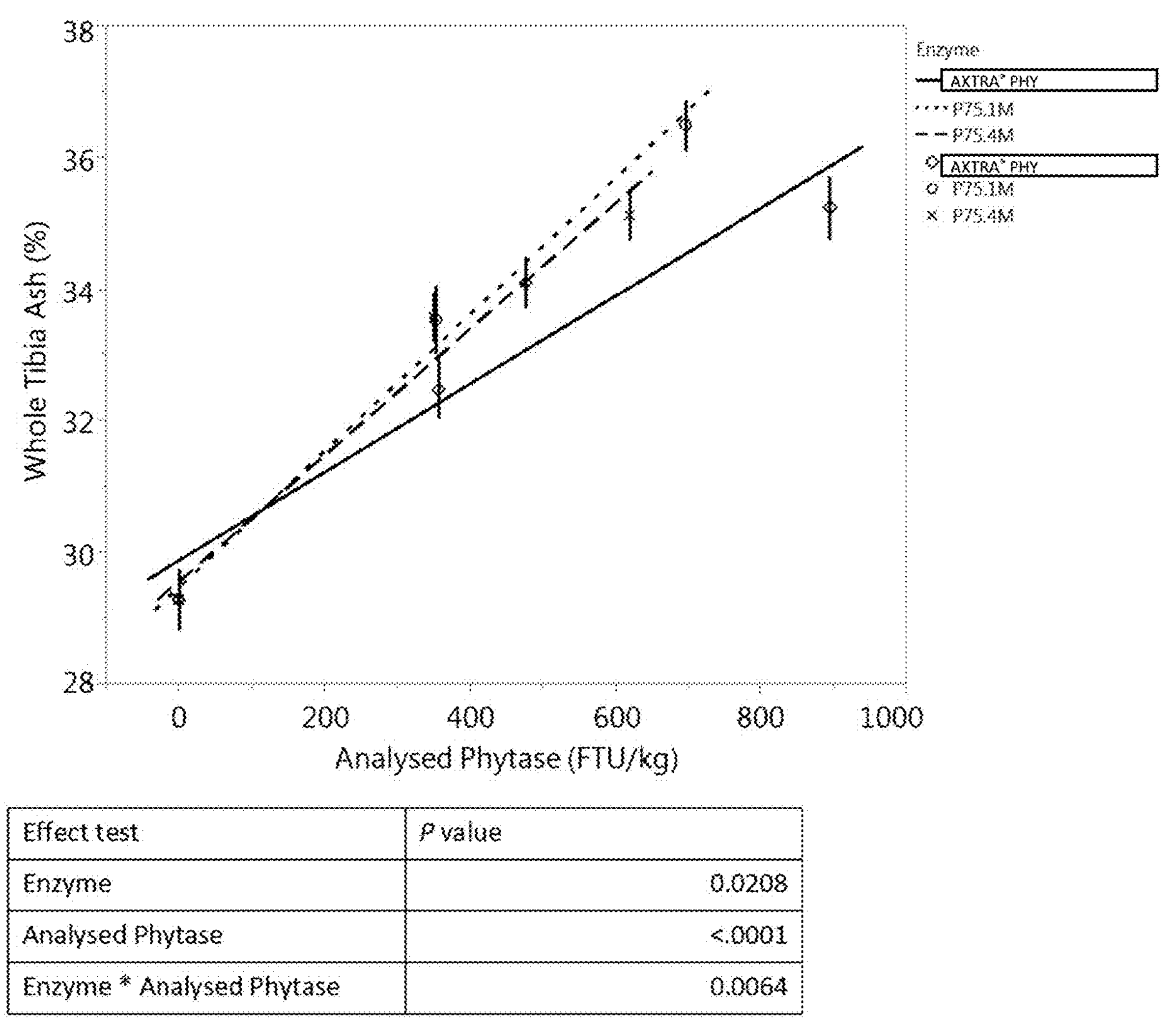
FIG. 11 is a graph showing the variation of whole tibia ash with measured in a feed phytase bioefficacy study using the same granules as in FIG. 7.
Figure 12:
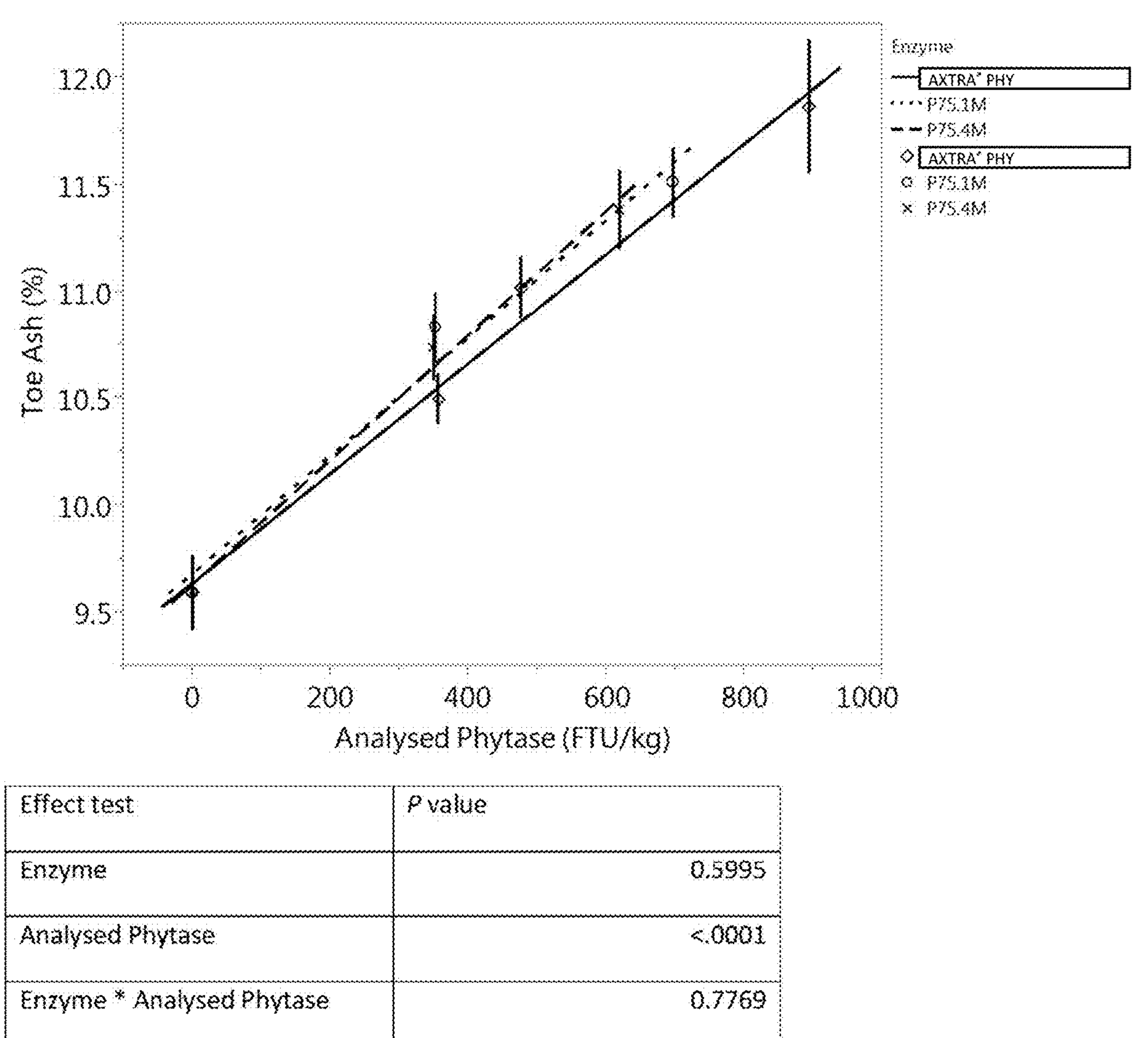
FIG. 12 is a graph showing the variation of toe ash with measured in a feed phytase bioefficacy study using the same granules as in FIG. 7.

FIGS. 10-12 show, respectively, the variation of epiphyseal tibia ash, whole tibia ash, and toe ash with measured in-feed phytase activity in study B. The results obtained for the epiphyseal tibia ash and whole tibia ash indicated that there was a significant difference in the bioavailability of the enzyme between the different formulations, whereby P75.1M and P75.4M demonstrated higher levels of bioavailability compared to the commercial AXTRA® PHY product. Based on the toe ash results, there was no significant difference in the bioavailability of the enzyme between the formulations P75.1M, P75.4M and the AXTRA® PHY. There was a significant effect of phytase on bone ash, whereby higher inclusion levels of enzyme resulted in higher bone ash.

Figure 13:
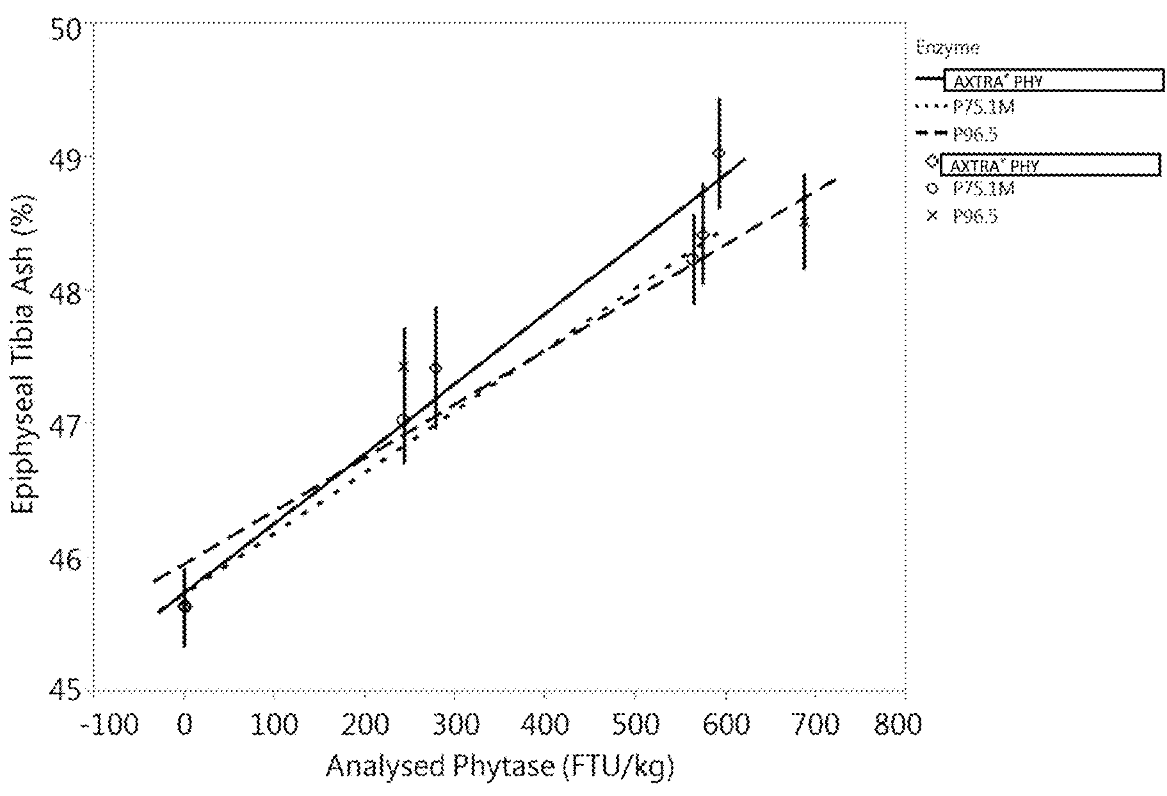
FIG. 13 is a graph showing the variation of epiphyseal tibia ash with measured in a feed phytase bioefficacy study. Test phytase granules were polyethylene wax-microencapsulated phytase granules P75.1M and P96.5. Commercial Danisco AXTRA® PHY product granules served as a control.
Figure 14:
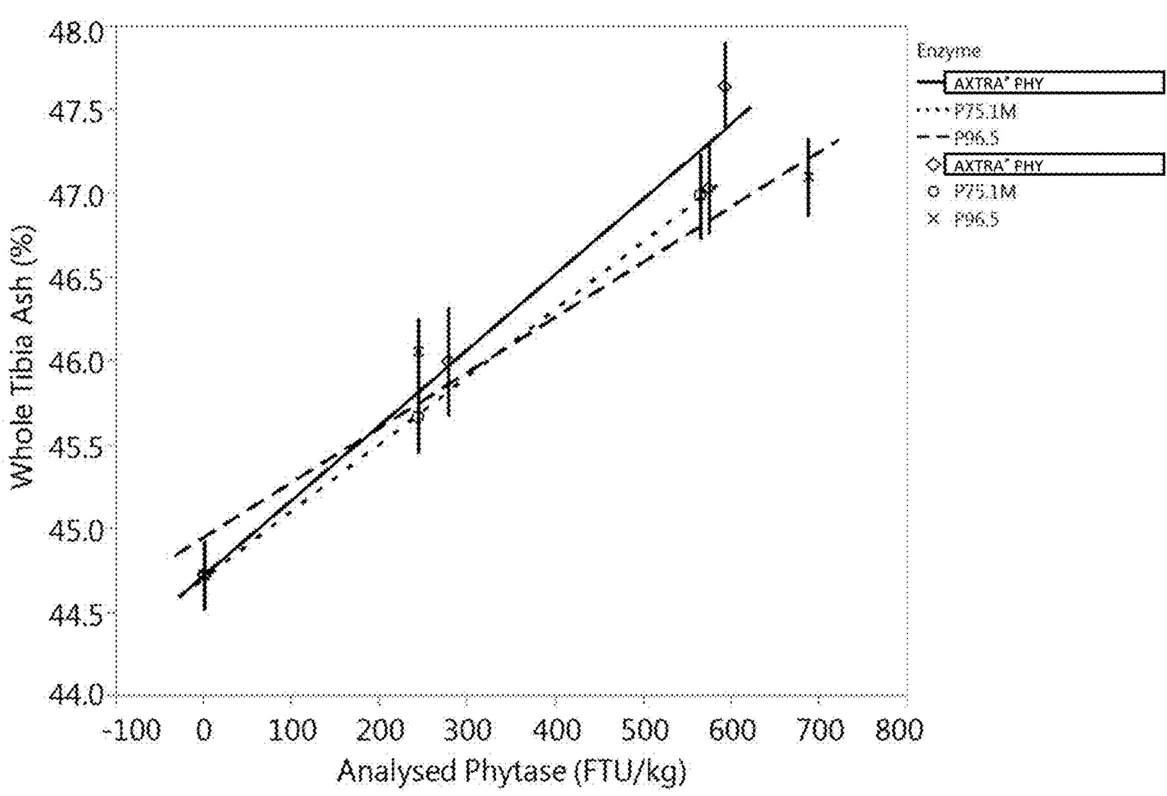
FIG. 14 is a graph showing the variation of whole tibia ash with measured in a feed phytase bioefficacy study using the same granules as in FIG. 13.
Figure 15:
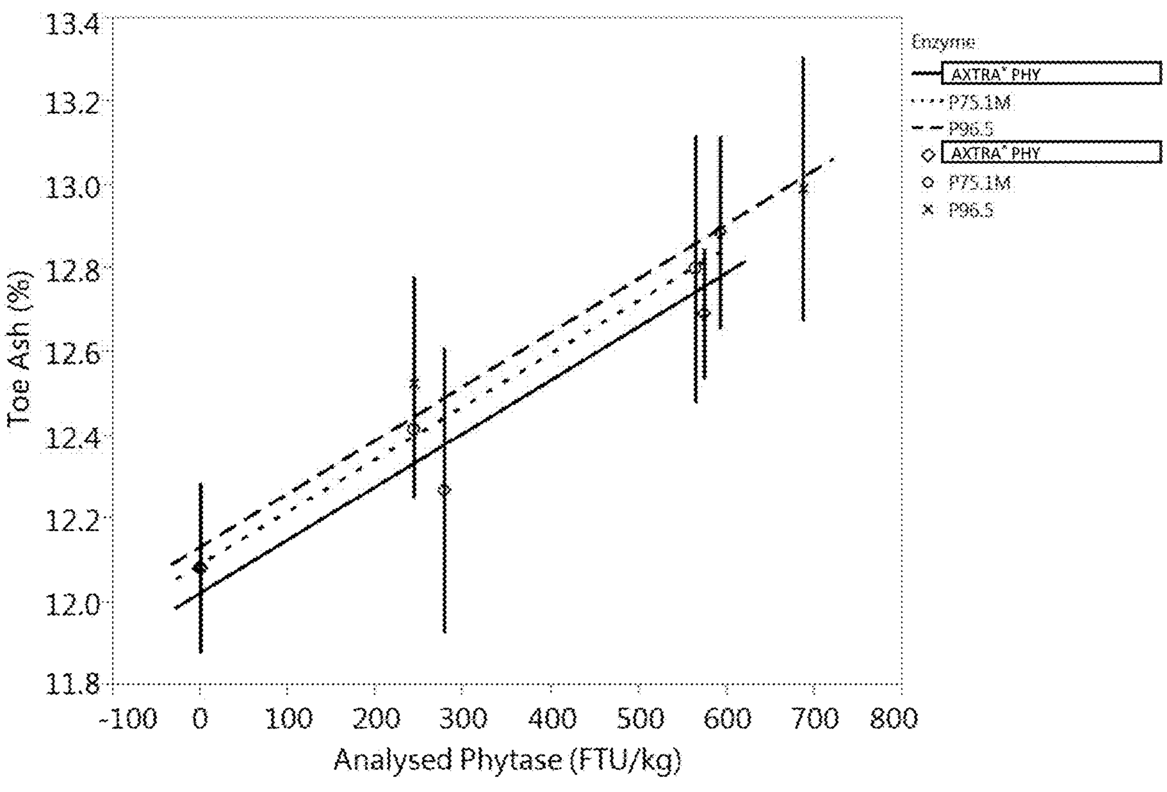
FIG. 15 is a graph showing the variation of toe ash with measured in-feed phytase activity in bioefficacy study using the same granules as in FIG. 13.

FIGS. 13-15 show, respectively, the variation of epiphyseal tibia ash, whole tibia ash, and toe ash with measured in-feed phytase activity in study C. The results obtained for the epiphyseal tibia ash, whole tibia ash, and toe ash indicated that there was no significant difference in the bioavailability of the enzyme between formulations P75.1M, P96.5 and the AXTRA® PHY. There was a significant effect of phytase on bone ash, whereby higher inclusion levels of enzyme resulted in higher bone ash.

Example 14. Bioefficacy Study of Polyethylene Wax-Microencapsulated Phytase Granules in Pigs An in vivo study was conducted to evaluate and compare the bioefficacy of phytase granule formulations P75.1M and P75.4M, produced with hot-melt spinning disk atomization (see Example 13). The bioefficacy of PE wax-microencapsulated phytase granules was compared with that of commercial AXTRA® PHY product.

A total of 70 pigs (16.82±1.34 kg initial BW) were allotted to a randomized complete block design with 7 diets and 10 replicate pigs per diet and two periods. The control diet was formulated with corn and soybean meal (SBM) and no phytase was added to this diet. The other six diets were similar to the control diet with the exception that phytase was included in the diet (Table 19). Diets were fed in mash form and were formulated to meet or exceed NRC (National Research Council) standards, except for Ca and AvP (Table 20).

TABLE 19

| Experimental design for studies HB1304 | | |
|---|---|---|
| Dosage | Dietary treatment | Phytase level (FTU/kg) |
| 1 | Negative control (NC) | 0 |
| 2 | NC + AXTRA ® PHY | 300 |
| 3 | NC + AXTRA ® PHY | 600 |
| 4 | NC + P75.1M | 300 |
| 5 | NC + P75.1M | 600 |
| 6 | NC + P75.4M | 300 |
| 7 | NC + P75.4M | 600 |

TABLE 20

| Diet formulations | |
|---|---|
| Ingredient | Inclusion (%) |
| Corn | 65.72 |
| Soybean meal (48% CP) | 30.00 |
| Limestone | 0.96 |
| L-Lys HCl | 0.41 |
| DL-Met | 0.09 |
| L-Thr | 0.12 |
| Choice white grease | 2.00 |
| Salt | 0.40 |
| Standard vitamin premix | 0.30 |
| Analyzed composition | |
| Dry matter, % | 89.60 |
| Ash (%) | 4.64 |
| Ca (%) | 0.66 |
| Phosphorus (%) | 0.34 |

In each period, after 5 days of adaptation, fecal samples were collected on day 6-12 and analyzed for phosphorous (P) using the total collection method. Pigs were fed at a daily level of 3 times the maintenance requirement for energy (i.e., 197 kcal ME per kg $BW^{0.60}$; NRC, 2012) divided into 2 equal meals. Water was available at all times throughout the experiment. Pig weights were recorded at the beginning of the adaptation period (day 0) and at the end of each collection period (day 13). The amount of feed supplied each day during the collection period was also recorded.

The beginning and end of fecal collection were marked by the addition of an indigestible marker. At the conclusion of the experiment, fecal samples were dried in a forced-air oven and finely ground before analysis. Diets, ingredients, and fecal samples were analyzed for P and apparent total tract digestibility (ATTD) of P % was calculated from the equation: ATTD P (%)=[(Pin−Pfo)/Pi]×100, wherein Pi is the total intake of P from day 6 to 12, and Pf is the total fecal output of P originating from the feed that was consumed from d 6 to 12. Data were analyzed using ANOVA, and means separation conducted to test differences between the different enzymes and enzyme doses. Pig was used as the experimental unit.

Figure 16:
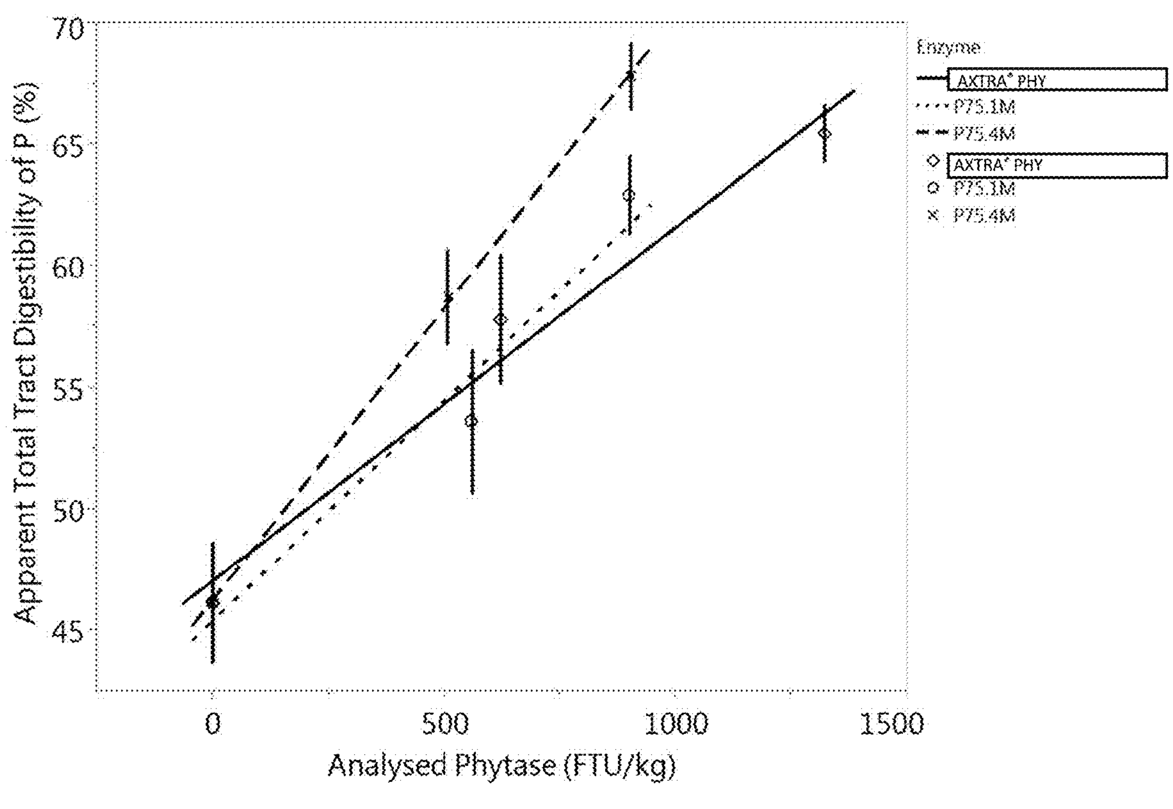
FIG. 16 is a graph showing the variation of apparent total tract digestibility of P % (ATTD P %) measured in a feed phytase bioefficacy study using the same granules as in FIG. 7.

As shown in FIG. 16, there was a significant effect of enzyme on Apparent Total Tract Digestibility of P % (ATTD P %), whereby P75.4M demonstrated higher ATTD P % than P75.1M and the commercial AXTRA® PHY product, suggesting a higher level of bioavailability for the formulation P75.4M.

Based on the results of Examples 13 and 14, it is apparent that the performance of the high-melting PE wax compositions was, in all instances, equal to or greater than the commercial AXTRA® PHY product in terms of the bioavailability markers investigated.

What is claimed is:

1. A particle for steam pelleting comprising particulates containing one or more enzymes dispersed within a high-melting wax matrix, wherein the high-melting wax matrix comprises a high-melting, water-insoluble wax having an onset melting point of at least 110° C. and a peak maximum melting point of at least 120° C. and an enthalpy change ratio between 40° C. and 140° C. ($ECR_{40,140}$) of less than 20% and wherein the high-melting, water-insoluble wax has a polydispersity index of less than 3, wherein the high melting, water-insoluble wax is a polyethylene wax and wherein said high-melting, water-insoluble wax constitutes 60-90% w/w of the said wax matrix.

2. The particle of claim 1 wherein the water-insoluble wax has a melt viscosity of less than 500 centipoises at temperatures within 25° C. above the wax melting temperature.

3. The particle of claim 2 wherein the water-insoluble wax has a weight average molecular weight of less than 3,000 Da (g/mol).

4. The particle according to claim 3 wherein the enzyme is at least one of amylase, cellulase, phytase, protease, or xylanase.

5. The particle according to claim 4 wherein the amount of active enzyme is greater than 5% wt/wt, and the active enzyme has a water activity of less than 0.3.

6. The particle according to claim 5 wherein the particulates range from about 1 to about 250 micrometers.

7. The particle of claim 3 wherein the water-insoluble wax has an $ECR_{(40,140)}$ of less than 15%.

8. The particle according to claim 1 comprising a water content of less than 5% wt/wt, and a water activity of less than 0.4.

9. The particle according to claim 8 wherein the particulates range from about 100 to about 500 micrometers.

10. The particle of claim 9 wherein the particulates range from about 212 to about 425 micrometers.

11. The particle of claim 9 wherein the particulates range from about 212 to about 300 micrometers.

12. The particle according to claim 11 wherein the particulates are produced with any of spray drying, spray chilling, dry granulation, wet granulation, or fluid bed granulation.

13. The particle according to claim 12 further comprising a filler ingredient selected from a group of mineral substances consisting of limestone, mica, clay, and titanium oxide.

14. The particle according to claim 13 wherein the particle further comprises a polyterpene resin, a rosin resin, damar gum, or a mixture of the said resins.

* * * * *